United States Patent
Wolf

(10) Patent No.: US 12,121,214 B2
(45) Date of Patent: Oct. 22, 2024

(54) APPARATUS AND METHOD FOR PLACEMENT OF DEVICE ALONG WALL OF A BODY LUMEN

(71) Applicant: University of Maryland, Baltimore, Baltimore, MD (US)

(72) Inventor: Jeffrey S. Wolf, Owings Mills, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 24 days.

(21) Appl. No.: 17/515,863

(22) Filed: Nov. 1, 2021

(65) Prior Publication Data

US 2022/0192672 A1   Jun. 23, 2022

Related U.S. Application Data

(63) Continuation of application No. 15/359,884, filed on Nov. 23, 2016, now Pat. No. 11,197,678, which is a
(Continued)

(51) Int. Cl.
*A61B 1/005* (2006.01)
*A61B 1/018* (2006.01)
(Continued)

(52) U.S. Cl.
CPC .............. *A61B 1/018* (2013.01); *A61B 1/267* (2013.01); *A61B 1/2733* (2013.01);
(Continued)

(58) Field of Classification Search
CPC ......... A61B 1/018; A61B 1/267; A61B 1/005; A61B 17/1204; A61B 17/12104;
(Continued)

(56) References Cited

U.S. PATENT DOCUMENTS

| | | |
|---|---|---|
| 3,996,938 A | 12/1976 | Clark |
| 4,921,484 A | 5/1990 | Hillstead |

(Continued)

FOREIGN PATENT DOCUMENTS

| | | |
|---|---|---|
| EP | 0533511 A1 | 3/1993 |
| JP | 1588733 A1 | 10/2005 |

(Continued)

OTHER PUBLICATIONS

ISA/EP: Partial Supplementary Search Report, European Patent Application No. 16922379.9, dated Jun. 29, 2020, pp. 1-10.
(Continued)

*Primary Examiner* — Anh Tuan T Nguyen
*Assistant Examiner* — Rynae E Boler
(74) *Attorney, Agent, or Firm* — Wolter Van Dyke Davis, PLLC; Eugene J. Molinelli; Cian O'Brien

(57) ABSTRACT

An apparatus includes: a expandable structure formable into three dimensional shapes including a range of diameters and corresponding lengths; a movable component moveable between a range of positions effecting the range of diameters; and a mechanical linkage disposed between the movable component and the expandable structure. The expandable structure is configured to fit inside a working channel of an endoscope when the expandable structure is collapsed. The mechanical linkage is configured to move the collapsed expandable structure through the working channel to a selected location past a distal end of the endoscope and to increase and decrease a diameter of the expandable structure in response to changes in the position of the movable component when the expandable structure is at the selected location.

19 Claims, 20 Drawing Sheets

Related U.S. Application Data continuation-in-part of application No. PCT/US2016/033917, filed on May 24, 2016.

(60) Provisional application No. 62/166,836, filed on May 27, 2015.

(51) Int. Cl.

| | | |
|---|---|---|
| *A61B 1/267* | (2006.01) | |
| *A61B 1/273* | (2006.01) | |
| *A61B 17/00* | (2006.01) | |
| *A61B 17/02* | (2006.01) | |
| *A61B 17/12* | (2006.01) | |
| *A61B 17/22* | (2006.01) | |
| *A61B 17/24* | (2006.01) | |
| *A61B 17/50* | (2006.01) | |
| *A61F 2/20* | (2006.01) | |
| *A61M 16/04* | (2006.01) | |
| *A61M 25/09* | (2006.01) | |
| *A61B 17/221* | (2006.01) | |
| *A61B 17/34* | (2006.01) | |
| *A61B 90/00* | (2016.01) | |

(52) U.S. Cl.
CPC ...... *A61B 17/0218* (2013.01); *A61B 17/1204* (2013.01); *A61B 17/12104* (2013.01); *A61B 17/22032* (2013.01); *A61B 17/24* (2013.01); *A61B 17/50* (2013.01); *A61F 2/20* (2013.01); *A61M 16/0472* (2013.01); *A61M 25/09* (2013.01); *A61B 1/005* (2013.01); *A61B 2017/00323* (2013.01); *A61B 2017/0034* (2013.01); *A61B 2017/00358* (2013.01); *A61B 2017/0225* (2013.01); *A61B 2017/1205* (2013.01); *A61B 2017/22035* (2013.01); *A61B 2017/22044* (2013.01); *A61B 17/221* (2013.01); *A61B 2017/3405* (2013.01); *A61B 17/3478* (2013.01); *A61B 2090/3945* (2016.02)

(58) Field of Classification Search
CPC ............. A61B 2017/0034; A61F 2/20; A61M 16/0472; A61M 25/09
See application file for complete search history.

(56) References Cited

U.S. PATENT DOCUMENTS

| | | | | |
|---|---|---|---|---|
| 5,437,665 | A * | 8/1995 | Munro | A61B 18/14 606/41 |
| 5,957,900 | A * | 9/1999 | Ouchi | A61B 17/221 604/21 |
| 6,090,129 | A | 7/2000 | Ouchi | |
| 6,159,243 | A * | 12/2000 | Schouwenburg | A61B 17/24 606/108 |
| 6,190,394 | B1 * | 2/2001 | Lind | A61B 17/221 606/127 |
| 6,283,988 | B1 * | 9/2001 | Laufer | A61N 1/06 607/101 |
| 6,405,732 | B1 * | 6/2002 | Edwards | A61B 18/1233 606/41 |
| 6,464,665 | B1 | 10/2002 | Heuser | |
| 6,743,237 | B2 | 6/2004 | Dhindsa | |
| 8,096,943 | B2 | 1/2012 | Melville | |
| 9,101,383 | B1 | 8/2015 | Dostal | |
| 2005/0021077 | A1 | 1/2005 | Chin et al. | |
| 2006/0241345 | A1 | 10/2006 | Oishi et al. | |
| 2006/0247619 | A1 * | 11/2006 | Kaplan | A61B 18/1492 606/41 |
| 2007/0083194 | A1 * | 4/2007 | Kunis | A61B 18/1492 606/41 |
| 2011/0125132 | A1 * | 5/2011 | Krolik | A61M 25/10185 604/509 |
| 2012/0109120 | A1 | 5/2012 | McHugo | |
| 2012/0174931 | A1 | 7/2012 | Nilsson et al. | |
| 2014/0046230 | A1 | 2/2014 | Kappel et al. | |
| 2015/0045788 | A1 * | 2/2015 | Litscher | A61B 17/12104 606/41 |

FOREIGN PATENT DOCUMENTS

| | | |
|---|---|---|
| WO | 9741807 A1 | 11/1997 |
| WO | 2011084616 A3 | 7/2011 |
| WO | 2012058109 A1 | 5/2012 |
| WO | 2016191419 A1 | 12/2016 |

OTHER PUBLICATIONS

ISA/EP: Examination Report, European Patent Application No. 16800635.1, dated Jul. 6, 2020, pp. 1-8.

International Search Report and Written Opinion, International Patent Application No. PCT/US16/33917, mailed Aug. 25, 2016, pp. 1-8.

International Search Report and Written Opinion, International Patent Application No. PCT/US16/63495, mailed Mar. 24, 2017, pp. 1-11.

ISR/WO, International Search Report and Written Opinion, International Patent Application No. PCT/US2016033917, Jan. 17, 2019, Publisher: European Patent Office, Published in: DE.

\* cited by examiner

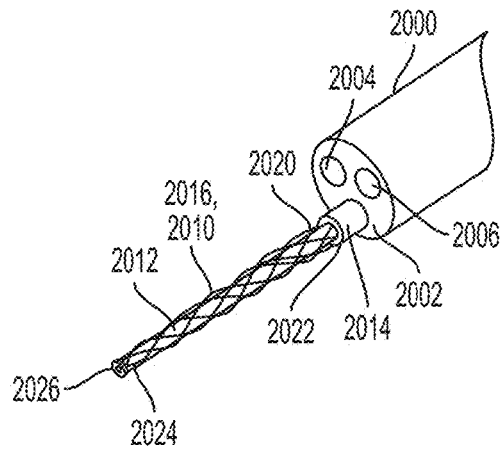
FIG. 20A
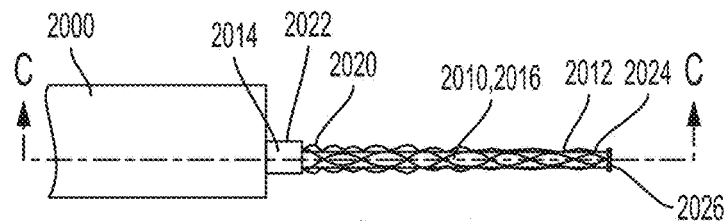
FIG. 20B
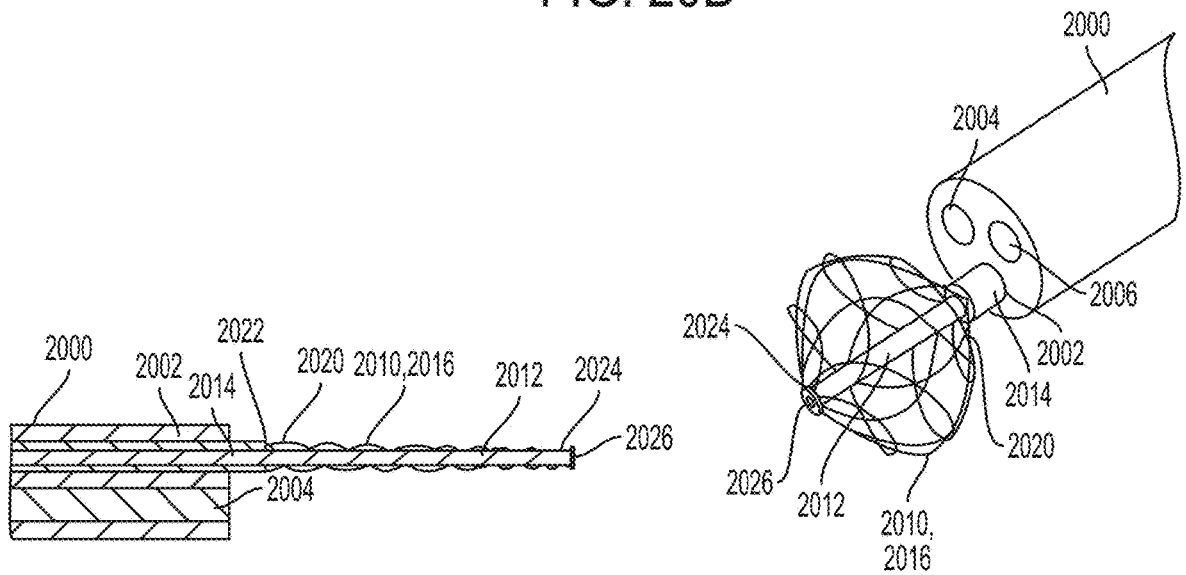
FIG. 20C
FIG. 20D

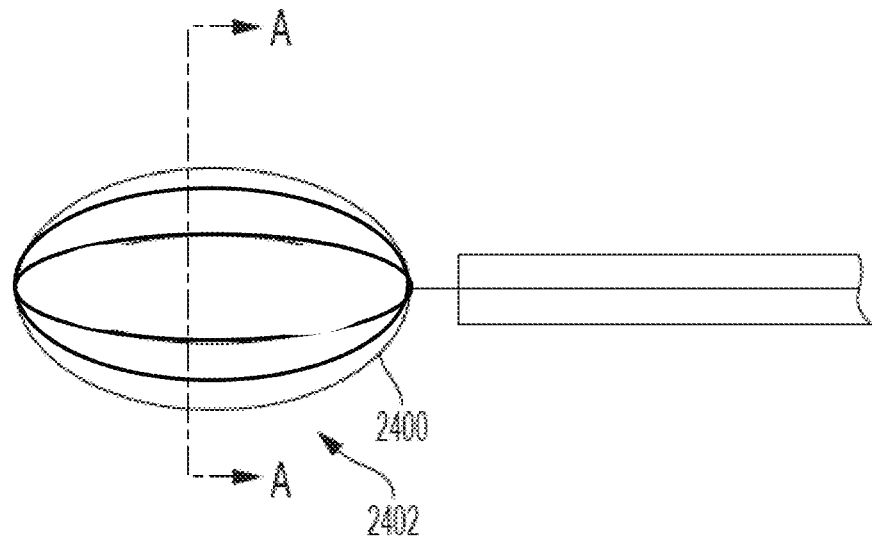
FIG. 24A
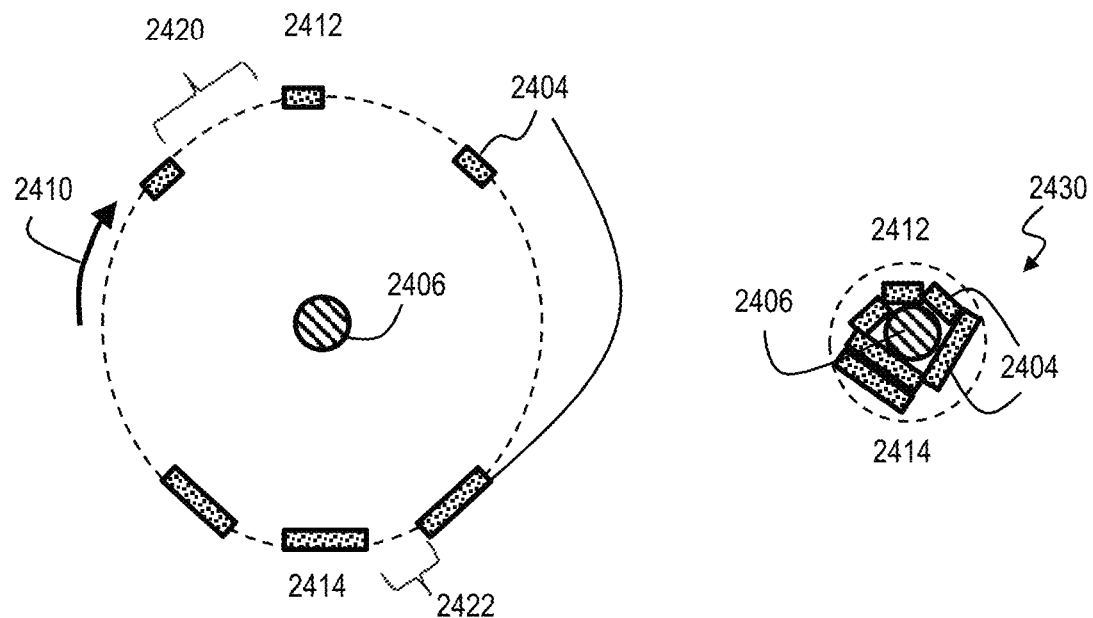
FIG. 24B
FIG. 24C

APPARATUS AND METHOD FOR PLACEMENT OF DEVICE ALONG WALL OF A BODY LUMEN

CROSS-REFERENCE TO RELATED APPLICATIONS

This application claims benefit as a Continuation-in-Part of International Appln. PCT/US2016/033917, filed May 24, 2016, the entire contents of which are hereby incorporated by reference as if fully set forth herein, under 35 U.S.C. § 120 of Provisional Application, which application claims benefit of U.S. provisional Appln. No. 62/166,836, filed May 27, 2015, the entire contents of which are hereby incorporated by reference as if fully set forth herein, under 35 U.S.C. § 119(e).

BACKGROUND

A laryngectomy is a medical procedure involving the removal of the larynx and separation of the airway from the mouth, nose and esophagus and creation of a stoma (artificial opening into a hollow organ) that allows air into the trachea through the neck. In a total laryngectomy the entire larynx is removed and in a partial laryngectomy only a portion is taken out. These procedures are usually performed in cases of laryngeal cancer. However, many laryngeal cancer cases are now treated only with more conservative surgeries through the mouth or with radiation and/or chemotherapy. Consequently, a laryngectomy is now generally performed when those treatments fail to conserve the larynx or there is sufficient destruction by the cancer that would prevent normal function of the larynx once the cancer is destroyed. Laryngectomies are also performed on individuals with other types of head and neck cancer or severe swallowing problems.

Voice functions in patients who have had a laryngectomy are generally achieved using a voice prosthesis that is placed in a tracheo-esophageal puncture between the trachea and the esophagus. The voice prosthesis is a one-way air valve that allows air to pass from the lungs/trachea to the esophagus when the patient covers the stoma. The redirected air vibrates the esophageal tissue producing a hoarse voice in lieu of the larynx.

Traditionally, the tracheo-esophageal puncture is created and a guide wire is inserted through the puncture using a rigid esophagoscope. The voice prosthesis is subsequently positioned in the tracheo-esophageal puncture with the help of the guide wire.

SUMMARY

The traditional procedure has a number of shortcomings. For example, it can be difficult or impossible to place a rigid esophagoscope in a patient who has had a laryngectomy due to scarring, and cervical spine mobility issues etc. In addition, the esophagus is in a collapsed state when the tracheo-esophageal puncture is created in the anterior wall of the esophagus. When collapsed, the posterior wall of the trachea is proximate, and may abut the anterior wall, putting it in close proximity with the needle puncturing the anterior wall. A great deal of caution must be exercised to avoid puncturing the posterior wall during the procedure. Accordingly, there remains room for improvement in the procedure and more generally, in the art related to placing an instrument or creating punctures through a wall of a body lumen.

A method and apparatus are disclosed for a placement of a device along a wall of a body lumen, such as placement of a puncturing instrument and or placement of a guidewire into puncture through the wall of the body lumen.

In a first set of embodiments, an apparatus includes a expandable structure formable into three dimensional shapes having a range of diameters and corresponding lengths; a movable component moveable between a range of positions effecting the range of diameters; and a mechanical linkage disposed between the movable component and the expandable structure. The expandable structure is sized/configured to fit inside a working channel of an endoscope when the expandable structure is collapsed. The mechanical linkage is configured to move the collapsed expandable structure through the working channel to a selected location past a distal end of the endoscope and to increase and decrease a diameter of the expandable structure in response to changes in the position of the movable component when the expandable structure is at the selected location.

In some embodiments of the first set, the mechanical linkage further includes an actuator cable secured to a distal end of the expandable structure. The actuator cable is configured to be pulled to effect movement of the distal end of the expandable structure toward a proximal end of the expandable structure to expand the expandable structure and to be pushed to effect movement of the distal end of the expandable structure away from the proximal end to collapse the expandable structure in response to movement of the movable component. The mechanical linkage may further include a hollow conduit surrounding the actuator cable.

In some embodiments of the first set, the mechanical linkage further includes a sheath. The sheath moves relative to the expandable structure in response to movement of the movable component. Movement of the sheath that exposes the expandable structure permits the expandable structure to expand under a natural resilience of the expandable structure, and movement of the sheath that envelope the expandable structure collapses the expandable structure against the natural resilience.

In some embodiments of the first set, the endoscope includes a flexible endoscope, and the mechanical linkage is characterized by a resilience that enables the mechanical linkage to flex with the flexible endoscope.

In a second set of embodiments, a system includes a flexible endoscope comprising a working channel; a expandable structure; a handle; and a flexible mechanical linkage disposed between the handle and the expandable structure. The mechanical linkage is configured to: deliver the expandable structure through the working channel to a location beyond the working channel; to increase a diameter of the expandable structure at the location in response to a first input from the handle; and to decrease the diameter of the expandable structure at the location in response to a second input from the handle. In some embodiments of the second set, decreasing the diameter is effective to capture an object disposed in an opening of the expandable structure.

In some embodiments of the second set, the handle further includes a movable component, wherein the first input includes movement of the movable component in a first direction and the second input includes movement of the movable component in a second direction different than the first direction.

In some embodiments of the second set, the mechanical linkage further includes a flexible actuator cable secured to a distal end of the expandable structure and configured to be pulled to effect movement of the distal end toward a proximal end of the expandable structure in response to the first input to expand the expandable structure. The actuator cable is also configured to be pushed to effect movement of the distal end away from the proximal end in response to the second input to collapse the expandable structure.

In some embodiments of the second set, the mechanical linkage further includes a sheath and actuator cable together configured to: move the expandable structure out of the sheath in response to the first input, thereby enabling the expandable structure to expand via a natural resilience of the expandable structure; and to retract the expandable structure into the sheath in response to the second input and against the natural resilience, thereby collapsing the expandable structure.

In some embodiments of the second set, the expandable structure includes a mesh comprising a plurality of elongated filaments that cooperate to enable the increasing and decreasing of the diameter of the expandable structure.

In some embodiments of the second set, a magnitude of the increase in the diameter is proportional to a magnitude of the first input, and a magnitude of the decrease in the diameter is proportional to a magnitude of the second input.

In a third set of embodiments, a method includes: inserting a flexible endoscope into a body lumen; inserting a expandable structure through a working channel in the endoscope to a location past a distal end of the endoscope; expanding the expandable structure, thereby imparting radial force to the body lumen and expanding the body lumen at the location of the expandable structure.

In some embodiments of the third set, the body lumen is an esophagus and the method includes piercing the esophagus with a puncture device while the expandable structure is expanded. In some of these embodiments, the method includes inserting a flexible guide wire through the puncture device and into the expandable structure while the expandable structure is expanded. In some of these embodiments, the method includes collapsing the expandable structure to capture the flexible guide wire therein. In some of these embodiments, the method includes removing the expandable structure while the flexible guide wire is captured in the collapsed expandable structure.

In a fourth set of embodiments, an apparatus includes a expandable structure formable into three dimensional shapes having a range of diameters and corresponding lengths, wherein the expandable structure is sized to fit inside a working channel of an endoscope when the expandable structure is collapsed; a movable component moveable between a range of positions effecting the range of diameters; and a means for expanding the expandable structure disposed between the movable component and the expandable structure, wherein the means is configured to move the collapsed expandable structure through the working channel to a selected location past a distal end of the endoscope and to increase and decrease a diameter of the expandable structure in response to changes in the position of the movable component when the expandable structure is at the selected location.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which:

FIG. 20A through FIG. 20F are diagrams that illustrate an example expandable structure using a wire mesh, according to another embodiment;

FIG. 24A through 24C are diagrams that illustrate an example expandable structure having backside protection, according to another embodiment.

DETAILED DESCRIPTION

Figure 1:
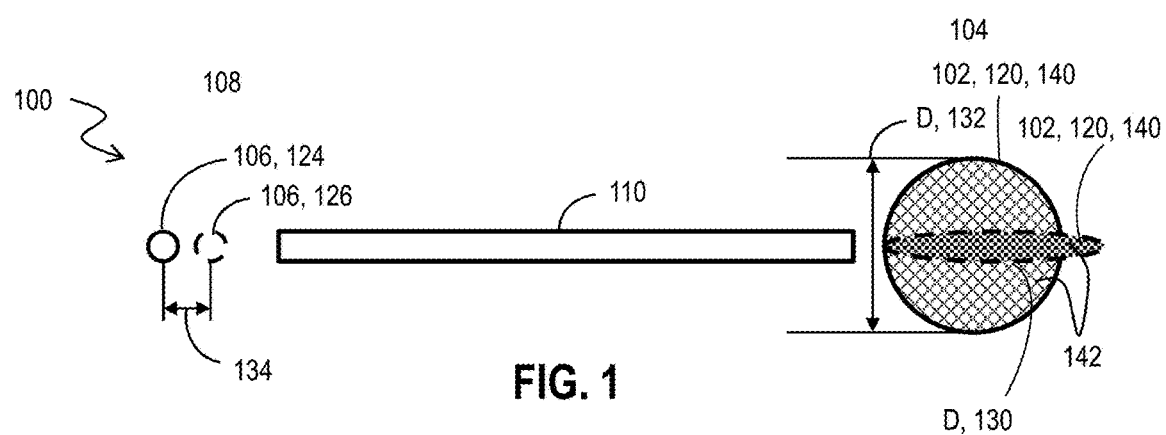
FIG. 1 schematically depicts an example embodiment of an apparatus for placement of a trachea-esophageal prosthesis.

A method and apparatus are described for an apparatus and method for placement of wire through a wall of a body lumen. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of forming a tracheo-esophageal puncture and placement of a voice prosthesis. However, the invention is not limited to this context. In other embodiments apparatus and method are used to support any body lumen or cavity, including, but not limited to a windpipe, a stomach, an intestine, a colon, a vein, and an artery, among others, e.g., for placing percutaneous feeding tube in the stomach or small bowel.

1. Overview

A unique and innovative apparatus and method have been devised for locating a device along a wall of a body lumen, such as for puncturing or placing a guide wire through a wall of a body lumen. The apparatus and method may be used in a range of procedures including, but not limited to placement of a guide wire subsequently used to aid in the placement of a voice prosthesis in post laryngectomy patients. The disclosed apparatus provides any one or more of several functions, including but not limited to: distending a lumen wall; providing support to counter forces that would tend to collapse the lumen wall; isolating one portion of the lumen wall from another; safely puncturing one wall of the lumen, and capturing an object present in or inserted into the lumen. In an example embodiment, the apparatus includes an expandable structure at a distal end that expands and contracts to achieve the above functions, plus a handle at a proximate end, and a link therebetween. In an example embodiment, the expandable structure is an expandable mesh. In addition, the apparatus is flexible and may be part of a system that includes the apparatus and a flexible endoscope and/or an esophagoscope.

Figure 15A:
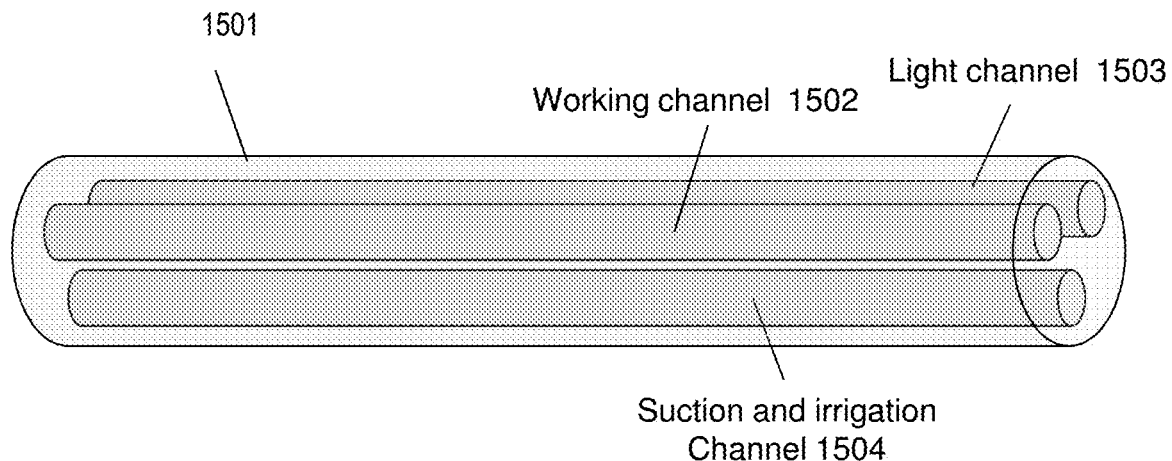
FIG. 15A and FIG. 15B are block diagrams that illustrate an example prior art flexible endoscope used in a system embodiment.
Figure 15B:
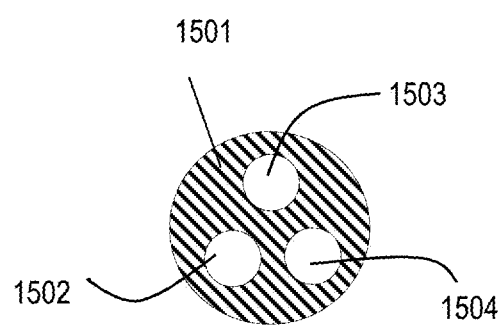

An endoscope is a flexible instrument used to examine the interior of a hollow organ or cavity (collectively referenced herein as a lumen) of the body. Endoscopes commonly include plural channels therethrough. FIG. 15A and FIG. 15B are block diagrams that illustrate an example prior art flexible endoscope 1501 used in a system embodiment For example, an endoscope 1501 may include a light channel 1503 to house a light source and/or camera used to light and visualize a target area. FIG. 15A presents a side view and FIG. 15B and end view. The endoscope may also include a suction and irrigation channel 1504 to control fluids at the target area. In addition, the endoscope may further include a working channel 1504 that may be used for placement of an instrument or prosthesis. Endoscopes may include more or fewer channels that have the same and/or different functions respectively. Gastroscopes are flexible endoscopes suited for use in the esophagus. Example endoscopes include, but are not limited to, the EVIS EXERA III GIF-HQ190 gastroscope manufactured by Olympus, and the i10 Series HD+, 90i Series HD Video, and the 90k Series video gastroscopes manufactured by Pentax Medical.

As a system, the endoscope may be inserted into the body lumen such that a distal end of the endoscope reaches a selected location. An apparatus that incudes an expandable mesh, such as described below with reference to FIG. 1, may be inserted through a working channel 1504 in the endoscope 1501 to position the expandable mesh portion of the apparatus at the selected location. The expandable mesh may then be expanded and collapsed at-will using a handle connected to the expandable mesh by a link such as a mechanical linkage. The camera using the light channel 1503 on the endoscope 1501 provides visualization not possible with a traditional rigid esophagoscope, thereby improving the procedure.

In an example embodiment the expandable mesh expands the lumen, as depicted below with reference to FIG. 4, then provides support for an anterior wall of the lumen against a collapsing force generated by a puncture device, such as a trocar or needle, that punctures the anterior wall of the lumen. Maintaining this support also keeps the posterior wall of the lumen away from the puncture site in the anterior wall. This reduces the chances of the puncture device traveling too far and harming the posterior wall. This also allows improved visualization of the entire prosthesis placement procedure from a camera in another working channel. The expandable mesh is then collapsed onto a guide wire or other device inserted through the site of the puncture and into the expandable mesh, as depicted below with reference to FIG. 5 and FIG. 6, thereby capturing the guide wire or other device in the expandable mesh. After the guide wire or other device is captured, the endoscope, the apparatus, and an end of the guide wire or other device may be retracted from the esophagus, as depicted below with reference to FIG. 7. The result is a guide wire or other device that enters the lumen through the puncture and exits the lumen through an opening used to insert the endoscope. In this example embodiment, the guide wire or device may then be used to help position a device in the vicinity of the puncture.

In an alternate example embodiment, instead of being inserted to the selected location through the working channel, the apparatus is inserted in parallel with the endoscope. In this manner the benefits provided by the endoscope, including the imaging and fluid control will be realized as will the benefits of the apparatus, but without the need to insert the apparatus through a working channel of the endoscope.

2. Example Embodiments

FIG. 1 schematically depicts an example embodiment of an apparatus 100 for placement of device along a body lumen. The apparatus includes an expandable structure 102 at a distal end 104, a movable component 106 at a proximal end 108, and a mechanical linkage 110 therebetween. The expandable structure 102 may be in an expanded state 120 or a collapsed state 122 in two or three dimensions. It is advantageous for the expandable structure 102 to expand in 3 dimensions in order to make it easier to locate and puncture the structure from outside the lumen in some embodiments, as described in more detail below. The movable component 106 is movable between a range of positions including a first position 124 associated with the expanded state 120 and a second position 126 associated with the collapsed state 122. Accordingly, the state of the expandable structure 102 may be controlled by moving the movable component 106 from one position to another position. In an example embodiment, moving the movable component 106 from the first position 124 to the second position 126 collapses the expandable structure 102. Similarly, moving the movable component 106 from the second position 126 to the first position 124 expands the expandable structure 102. In an example embodiment, a structure diameter D of the expandable structure, which includes a collapsed diameter 130 and an expanded diameter 132, is proportional to a location of the movable component 106 along the range of positions 134.

In some embodiment's, the structure has a natural unflexed state that is either the collapsed state or the expanded state or some intermediate state; and when the expandable structure is not constrained, that is, no substantial external forces are applied, the structure assumes its natural unflexed state and the movement component assumes a corresponding position.

Although the first position 124 and the second position 126 are shown on the left and right respectively, any other configuration may be used. For example, they may be reversed. Alternately, the movable component may be a rotary dial and the positions may be different angular positions of the rotary dial. Movement along the range of positions 134 may be accomplished by manual input, or via electrical or hydraulic mechanism etc.

Likewise, the mechanical linkage 110 may be a cable and conduit/sheath arrangement as disclosed below, or any other mechanical apparatus and may include cables, pulleys, levers, chains etc. Alternately, or in addition, the mechanical linkage may include electrical and/or hydraulic mechanisms that convey input from the movable component 106 to the expandable structure 102. In various embodiments described below where an element, such as an actuator cable, is pushed, the use of these mechanical linkages produces a result that can push or pull on a proximal or distal end or intermediate portion of the expandable structure. Similarly, in some embodiments below when an element is pulled, the use of these mechanical linkages produces a result that can pull or push on a proximal or distal end or intermediate portion of the expandable structure. In some embodiments, the mechanical linkage 110 may be a conduit that delivers a fluid such as a gas (e.g., air) or a liquid (e.g., a saline aqueous solution) to the expandable structure 102, which could be, for example, an inflatable element. In such embodiments, the movable component 106 would be replaced with a valve or switch that controls a flow of the fluid though the mechanical linkage 110 to and from the expandable structure 102.

In an example embodiment the expandable structure 102 comprises an expandable mesh 140. However, the expandable structure 102 need not be limited to an expandable mesh 140. The expandable structure 102 may any configuration capable of fitting inside a working channel of an endoscope when collapsed and also capable of expanding by an amount sufficient to distend/expand a lumen (e.g. an esophagus). In addition, once expanded, the expandable structure 102 should be structurally sufficient to support the distended lumen against forces that would tend to collapse the distended lumen.

Embodiments disclosed herein describe the expandable structure 102 as a expandable mesh, but another type of expandable structure could be substituted that is in keeping with the concepts presented herein. In an example embodiment, the expandable mesh is composed of filaments 142 of a flexible material. Example materials include coated metals, uncoated metals, and plastics. In an example embodiment the filaments 142 are composed of Nitinol® Wire manufactured by 3M Unitek™ of Monrovia, CA Other acceptable materials include floroplastics such as PTFE (PolyTetraFluoroEthylene), FEP (FluoroEthylenePropylene), PFA (Per Fluor Alkoxy), ETFE (Ethylene Tetra Fluoro Ethylene Copolymer), E-CTFE (Ethylene-Chloro Tri Fluoro Ethylene), PVDF (Poly Vinylidene Fluoride), and PVF (Polyvinyl Fluoride) and PTFE coated stainless steel wire. The filaments may be wound, spiraled, or configured in any arrangement that changes diameter in response to an input.

In an example embodiment, the filaments 142 are within their elastic deformation ranges when in the expanded state 120 as well as the collapsed state 122. In such an arrangement, an application of force changes the shape and associated diameter of the expandable mesh without harm to the expandable mesh 140. This enables repeated expansion and collapse of the expandable mesh 140 during a single procedure and reuse for different procedures without harm to the expandable mesh 140.

In an example embodiment, the filaments 142 are not within their elastic deformation ranges when in the expanded state 120 as well as the collapsed state 122. As a result, the expansion and/or collapse of the expandable mesh 140 will deform the filaments 142. This, in turn, will deform the expandable mesh 140. In instances when the expandable mesh 140 need not remain in its original state, this is acceptable. For example, the filaments 142 may be within their elastic range when the expandable mesh 140 is in the collapsed state 122. Upon expanding, the filaments 142 plastically deform such that full collapse into the original state is not possible. However, when collapse by an amount sufficient to capture a wire in the expandable mesh 140 is possible, the expandable mesh 140 is adequate. This is because in its original, fully collapsed state, the expandable mesh 140 must fit into the working channel of the endoscope for insertion to the location in the esophagus. The expandable mesh 140 need not fit back into the working channel once the wire is captured. Instead, the endoscope can be withdrawn from the esophagus with the partially collapsed expandable mesh 140 only partially retracted into the working channel, or not retracted at all, without any harm to the esophagus. The deformed expandable mesh 140 may then be discarded.

Flexible materials include a natural resilience, and the expandable mesh 140 may take advantage of a natural resilience of the filaments 142 in its construction. In an example embodiment, a resiliency of the expandable mesh 140 may urge the expandable mesh 140 into a shape termed a natural shape. As used herein, the natural shape of the expandable mesh 140 is the shape taken as part of the apparatus 100 in the absence of application of an external force. Accordingly, an application of external force changes the shape and associated diameter of the expandable mesh against the natural resilience of the expandable mesh 140. For example, the natural state may be one where the resilience of the filaments 142 urges the expandable mesh 140 into the collapsed state 122. Consequently, force is applied via the movable component 106 to expand the expandable mesh 140. Alternately, the natural state may be the expanded state 120, and force may be applied to collapse the expandable mesh 140. The natural state need not be limited to either the expanded state 120 or the collapsed state 122. Instead, the natural state may any shape in between. In such a configuration force is applied in one direction to expand the expandable mesh 140 from an intermediate natural position, and a different direction to collapse the expandable mesh 140 from the intermediate natural position.

Figure 16A:
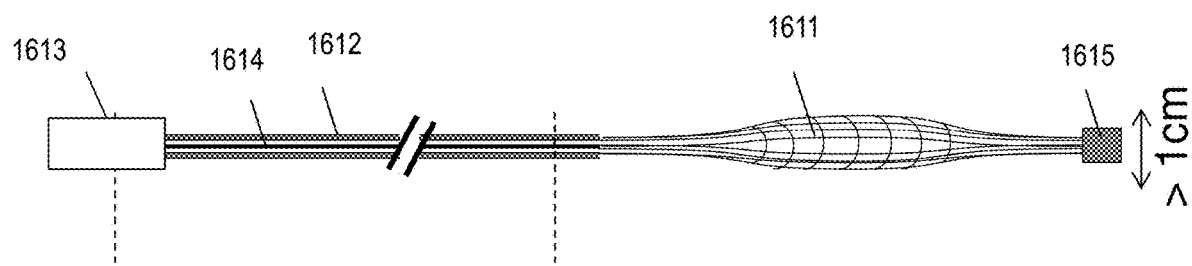
FIG. 16A and FIG. 16B are block diagrams that illustrate an example apparatus with collapsed and expanded expandable mesh, respectively, according to an embodiment.
Figure 16B:
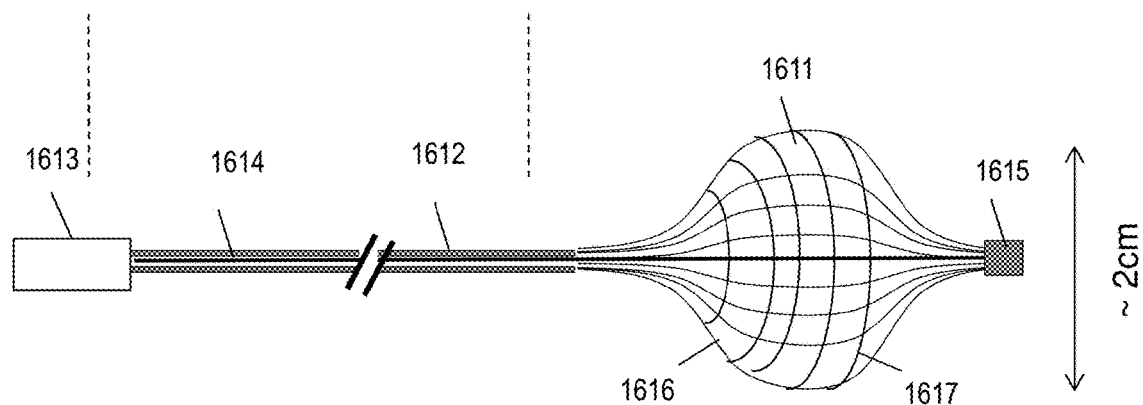

FIG. 16A and FIG. 16 are block diagrams that illustrate an example apparatus with collapsed and expanded expandable mesh, respectively, according to an embodiment. This embodiment includes a handle 1613, a tube 1612 and a cable 1614, with a distal end 1615 and an expandable mesh 1611. In this embodiment, the mesh 1611 comprises longitudinal filaments 1616 and transverse filaments 1617. In some embodiments, the transverse filaments 1617 provide a restorative force to return mesh 1611 to a natural collapsed state depicted in FIG. 16A. In some embodiments, the longitudinal filaments 1616 provide a restorative force to return the mesh 1611 to an expanded state depicted in FIG. 16B in stead of or in addition to the restorative force provided by transverse filaments 1617.

Figure 16C:
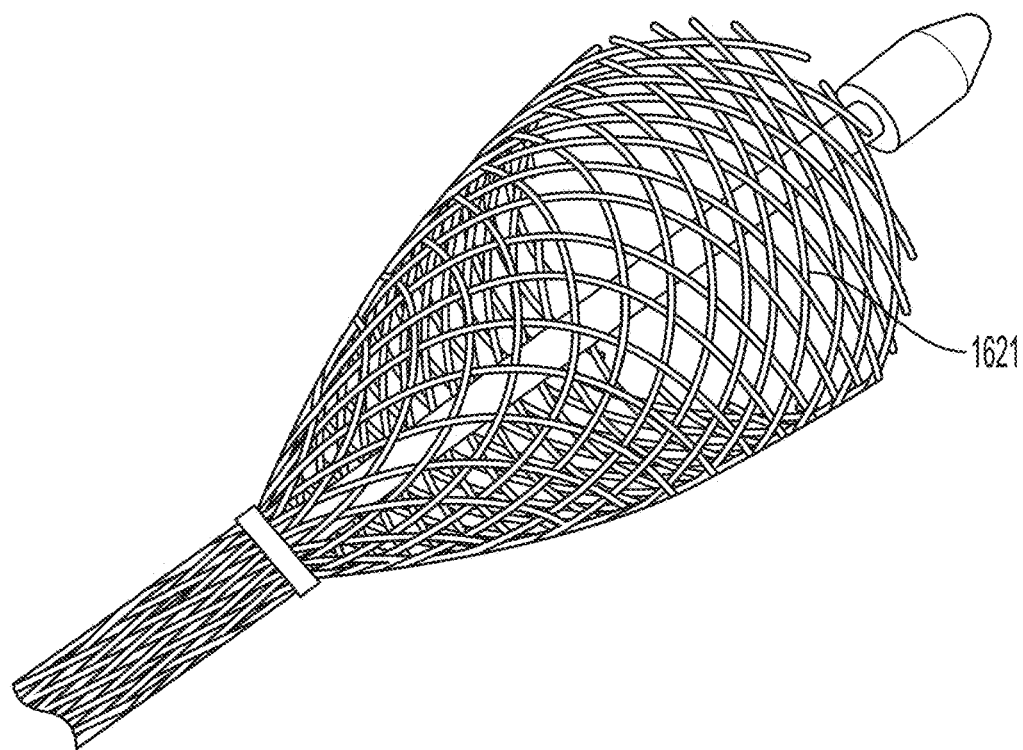
FIG. 16C is a block diagram that illustrates an example crisscrossed wire mesh in expanded state, according to an embodiment.
Figure 16D:
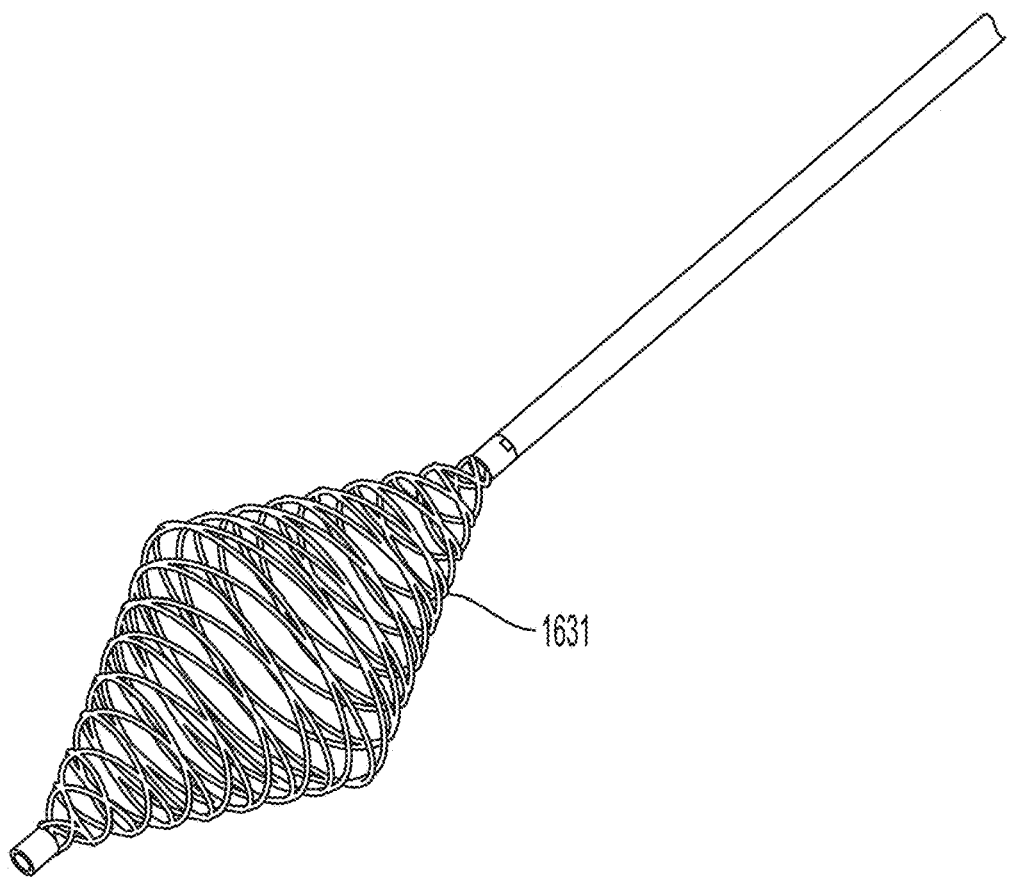
FIG. 16D is a block diagram that illustrates an example helix wire mesh in expanded state, according to an embodiment.
Figure 16E:
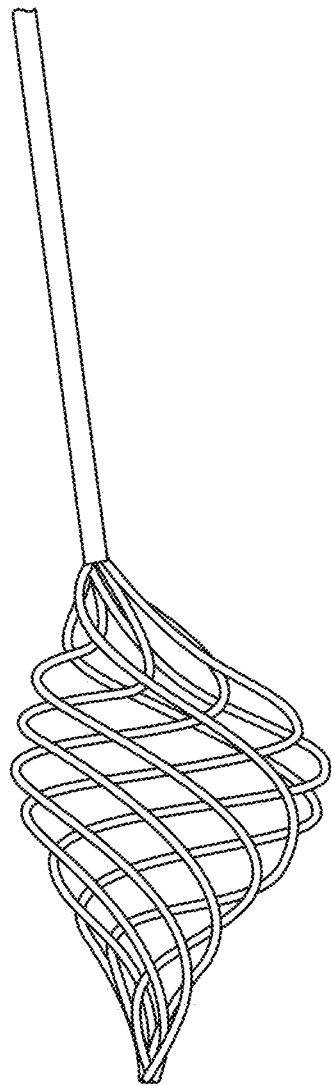
FIG. 16E and FIG. 16F are block diagrams that illustrate an example mesh in expanded state without and with a light source, respectively, according to various embodiments.
Figure 16F:
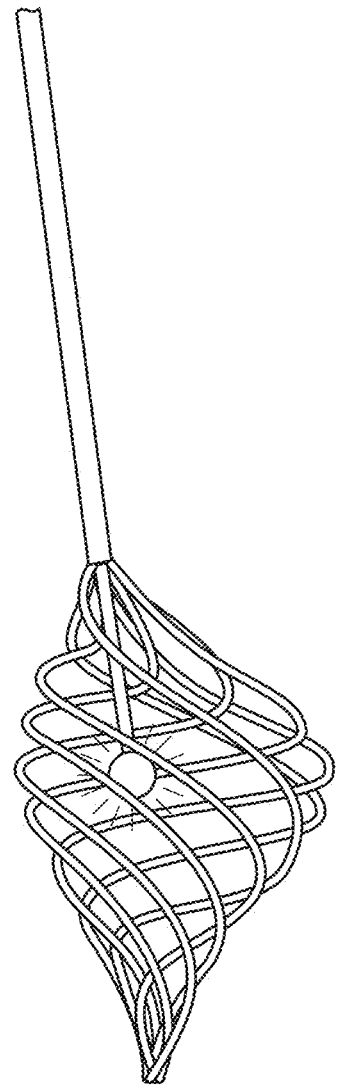
Figure 16G:
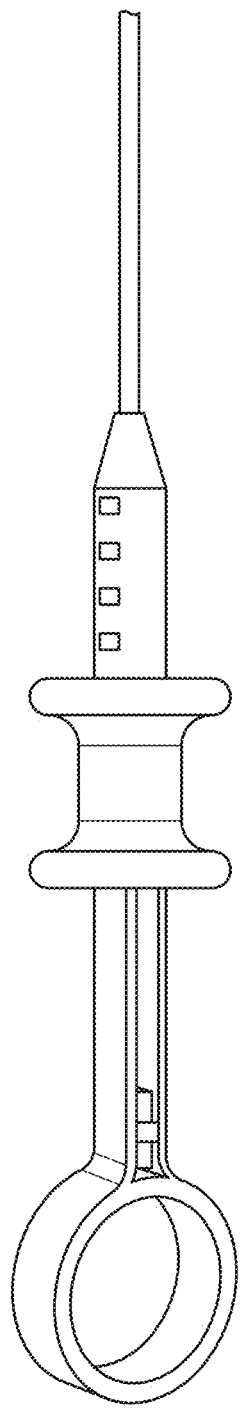
FIG. 16G is a block diagram that illustrates an example handle with a moveable ring as the moveable component, according to an embodiment.

FIG. 16C is a block diagram that illustrates an example crisscrossed wire mesh 1621 in expanded state, according to an embodiment. FIG. 16D is a block diagram that illustrates an example helix wire mesh 1631 in expanded state, according to an embodiment. FIG. 16E and FIG. 16F are block diagram that illustrate an example mesh in expanded state without and with a light source, respectively, according to various embodiments. FIG. 16G is a block diagram that illustrates an example handle with a moveable ring as the moveable component, according to an embodiment.

Figure 2:
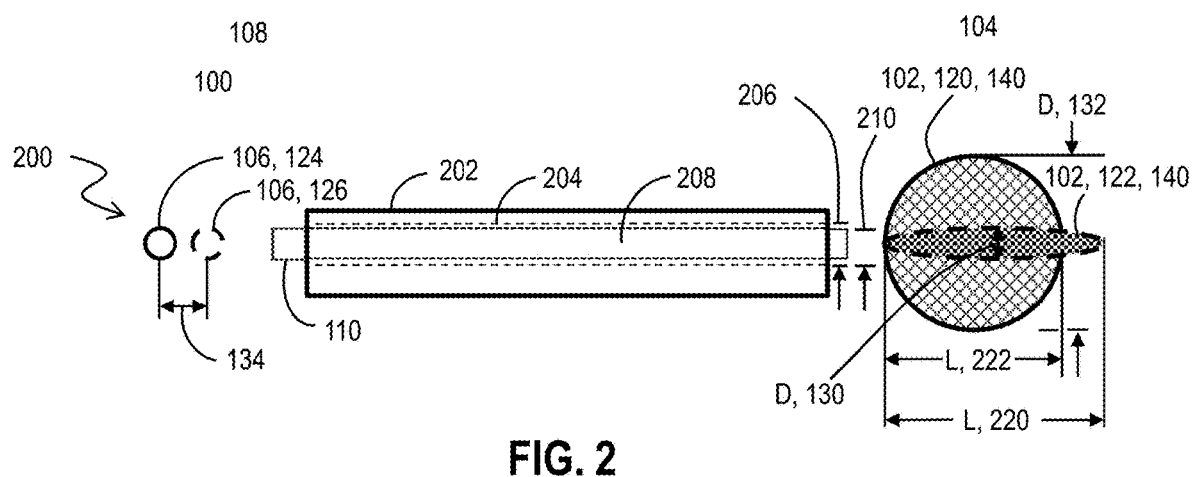
FIG. 2 schematically depicts a system including the apparatus of FIG. 1 and a flexible endoscope.

FIG. 2 schematically depicts a system 200 including the apparatus 100 of FIG. 1 and a flexible endoscope 202. Visible within the flexible endoscope 202 is a working channel 204 having an inner diameter that varies among endoscopes. Common working channel diameters 206 range in diameter up to about 2.8 to 3.0 millimeters. Consequently, those parts of the apparatus 100 inserted into the endoscope's working channel 204, including the expandable mesh in a collapsed state, are advantageously no larger than the working channel diameter 206 of the endoscope 202 being used. In an example embodiment, the expandable mesh 140 is characterized by a structure diameter 130 of less than about three (3) millimeters in the collapsed state 122. Similarly, at a portion of the mechanical linkage 110 that also fits into the working channel 204 is characterized by a linkage diameter 210 of less than about three (3) millimeters. In an example embodiment, the structure diameter 130 and the portion 208 of the mechanical linkage 110 are characterized by diameters less than about 2.5 millimeters.

The expandable mesh 140 is also characterized by a length L, including a collapsed length 220 and an expanded length 222. The lengths are not constrained by the working channel 204 and as such, can be selected primarily based on what is desirable to achieve the desired expanded diameter 132. In various embodiments, the expanded length 222 ranges from about 20 to about 80 millimeters. The collapsed length 220 ranges from about 20 to about 120 millimeters. The expanded diameter 132 ranges from about 10 to about 40 millimeters. The collapsed diameter ranges from about 1.5 to about 2.8 millimeters. In an example embodiment, an expanded length 222 of fifty (50) millimeters and a collapsed length 220 of about 80 millimeters are sufficient to achieve a collapsed diameter 130 of 2.5 millimeters and an expanded diameter 132 of twenty-five (25) millimeters using filaments characterized by a diameter of from about 0.1 to about 1 Millimeters (wire gauges from about 38 to about 18). These dimensions would be shifted to a scale appropriate for the body lumen, e.g., for an expanded diameter of 70 mm in a colon and an expanded diameter of about 5 mm in a carotid artery of a subject.

Figure 3:
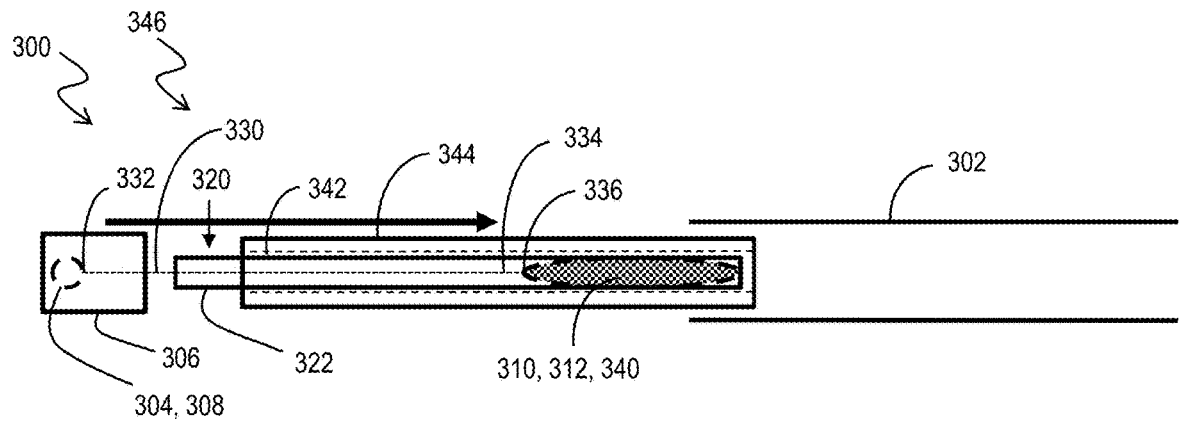
FIG. 3 schematically illustrates a step of inserting an example embodiment of the apparatus into an esophagus.

FIG. 3 through FIG. 7 schematically illustrates an example embodiment of the apparatus and its use. FIG. 3 schematically illustrates a step of inserting an example embodiment of the apparatus 300 into an esophagus 302. The apparatus 300 includes a movable component 304 disposed on a left side of the handle 306 and in a first position 308 associated with a collapsed state 310 of the expandable mesh 312. It is noted that the movements and positions of the movable component 304 are purely schematic and may be any type of movement in any direction. The mechanical linkage 320 includes a sheath 322 surrounding the expandable mesh 312 and also surrounding an actuator cable 330. The actuator cable 330 includes a proximate end 332 connected to the movable component 304 and a distal end 334 connected to a proximate end 336 of the expandable mesh 312. In this example embodiment, the natural state of the expandable mesh 312 is the expanded state. Consequently, the sheath 322 holds the expandable mesh 312 in the compressed state 310 against a resilience of the filaments 340. The apparatus 300 may be inserted into the working channel 342 of the endoscope 344 before, concurrent with, or after the endoscope 344 is inserted into the esophagus 302. Together the apparatus 300 and the endoscope 344 constitute the system 346.

Figure 4:
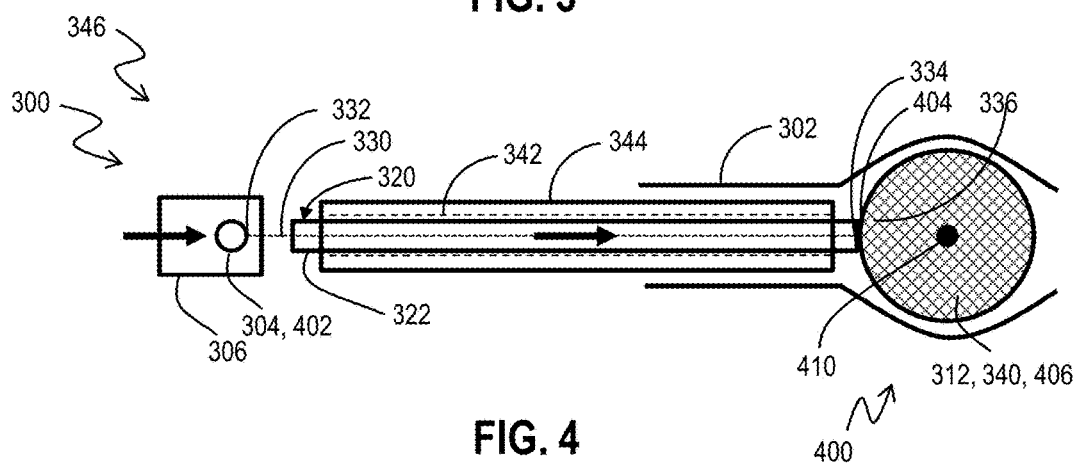
FIG. 4 schematically illustrates a step of expanding an expandable mesh of the apparatus of FIG. 3.

FIG. 4 schematically illustrates a step of expanding a expandable mesh 312 of the apparatus 300 of FIG. 3. Upon reaching a selected location 400 in the esophagus 302 the movable component 304 is moved to the right side of the handle 306 into a second position 402. This movement pushed the actuator cable 330 which, in turn, pushes the expandable mesh 312 past a distal end 404 of the sheath 322. Upon being exposed, the resilience of the filaments 340 expands the expandable mesh 312 into the expanded state 406, which is the natural state in this example embodiment. This action distends/expands the esophagus at the selected location 400. A light source 410 may be illuminated at an intensity that makes it visible from a location outside the esophagus. For example, the light source 410 may be visible through a wall of the esophagus when looking at the outside of the esophagus through a stoma. Alternately, or in addition, the endoscope 344 may have its own light source (not shown) that is similarly visible. This light source enables an operator to visibly determine the location of the expandable mesh 312 from outside the lumen; and, in some embodiments, visible even outside the body where the lumen is situated.

Figure 5:
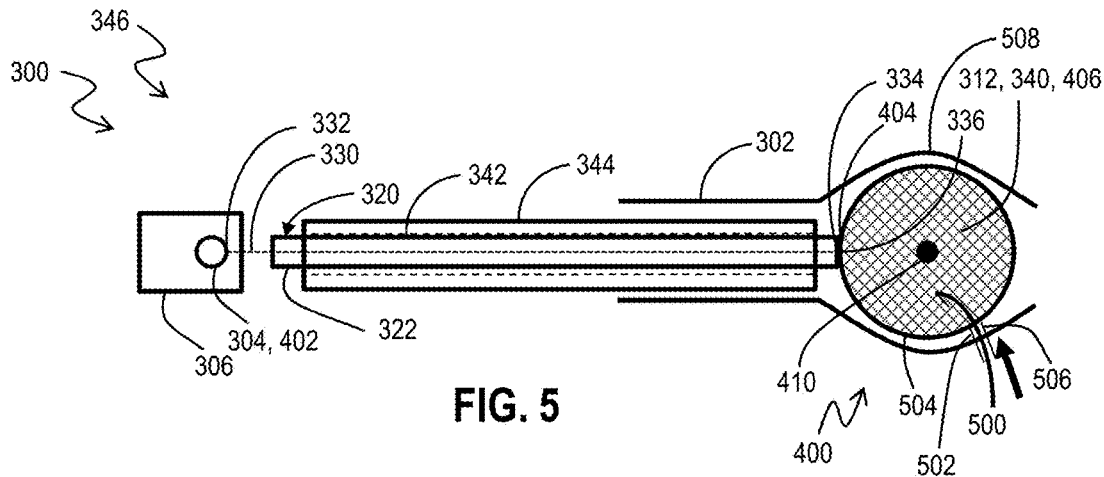
FIG. 5 schematically illustrates a step of inserting of a wire into the expanded expandable mesh of FIG. 4.

FIG. 5 schematically illustrates a step of inserting of a guide wire 500 into the expanded expandable mesh 312 of FIG. 4. The guide wire 500 is inserted through a tracheo-esophageal puncture 502 in an anterior wall 504 of the esophagus 302. In an example embodiment the tracheo-esophageal puncture 502 is first made using a hollow puncture needle 506. The wire 500 is fed into a hollow interior of the puncture needle 506 until the wire 500 passes into the expandable mesh 312. The puncture needle 506 remains in place in some embodiments, and is removed in other embodiments, once the wire 500 is inserted. In other embodiments, any other suitable device known to those in the art may be used in place of the shallow puncture needle 506, such as a trocar. Alternately, in some embodiments, the wire 500 may be inserted alone. In the expanded state 406, the expandable mesh 312 is characterized by openings between the filaments 340 that are large enough to permit the wire 500 to pass through the expandable mesh 312. In some embodiments, the needle is about a 14 gauge needle (1.6 mm inner diameter) and the flexible guide wire can be any size to fit through the needle, e.g., any higher gauge wire. The flexible wire material can be any suitable for feeding through the wall of the body lumen without sawing or tearing the wall, such as the materials recited above for the filaments or filament coating, including fluoroplastics such as PTFE (PolyTetraFluoroEthylene), FEP (FluoroEthylenePropylene), PFA (Per Fluor Alkoxy), ETFE (Ethylene Tetra Fluoro Ethylene Copolymer), E-CTFE (Ethylene-Chloro Tri Fluoro Ethylene), PVDF (Poly Vinylidene Fluoride), and PVF (Polyvinyl Fluoride) and PTFE coated stainless steel wire. In the expanded state 406, the expandable mesh 312 is also structurally strong enough to support the posterior wall 508 in a position away from the tracheo-esophageal puncture 502. This reduces the chances the puncture needle 506 will cause harm to the posterior wall 508.

Figure 6:
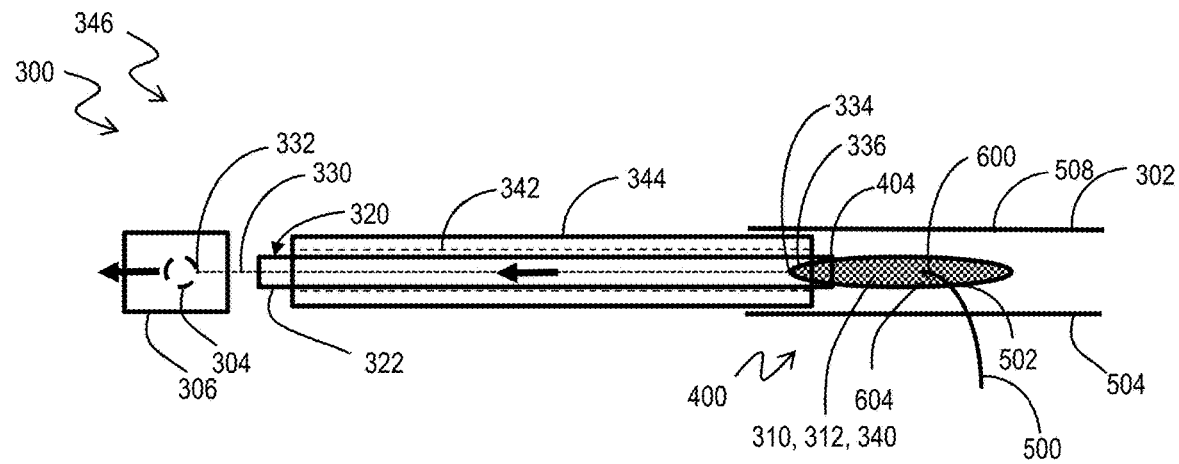
FIG. 6 schematically illustrates a step of collapsing the expandable mesh onto the wire of FIG. 5.

FIG. 6 schematically illustrates a step of collapsing the expandable mesh 312 onto the wire 500 of FIG. 5. The movable component 304 is moved back from the second position 402 toward the first position 308. This pulls on the actuator cable 330 which, in turn, begins to draw the proximate end 336 of the expandable mesh 312 back into the distal end 404 of the sheath 322. This action collapses the expandable mesh 312 until the expandable mesh 312 captures an end 600 of the wire 500. In the example embodiment (shown) the movable component 304 does not fully return to the first position 308 because the wire 500 in the expandable mesh 312 prevents full collapse. However, in an alternate example embodiment, the expandable mesh 312 fully collapses and is fully withdrawn, along with the end 600 of the wire, into the working channel 342. In some embodiments, the puncture needle 506 is removed at this step.

In an example embodiment, the wire 500 includes an interlocking feature 604 such as a hook or loop that interlocks with the filaments 340 of the expandable mesh 312, thereby improving the capture. In an embodiment, once the expandable mesh 312 is collapsed, the interlocking feature will assume a benign orientation such as parallel to the esophagus walls. This will reduce the chances of harm to the esophagus walls from dragging during extraction from the esophagus.

Figure 7:
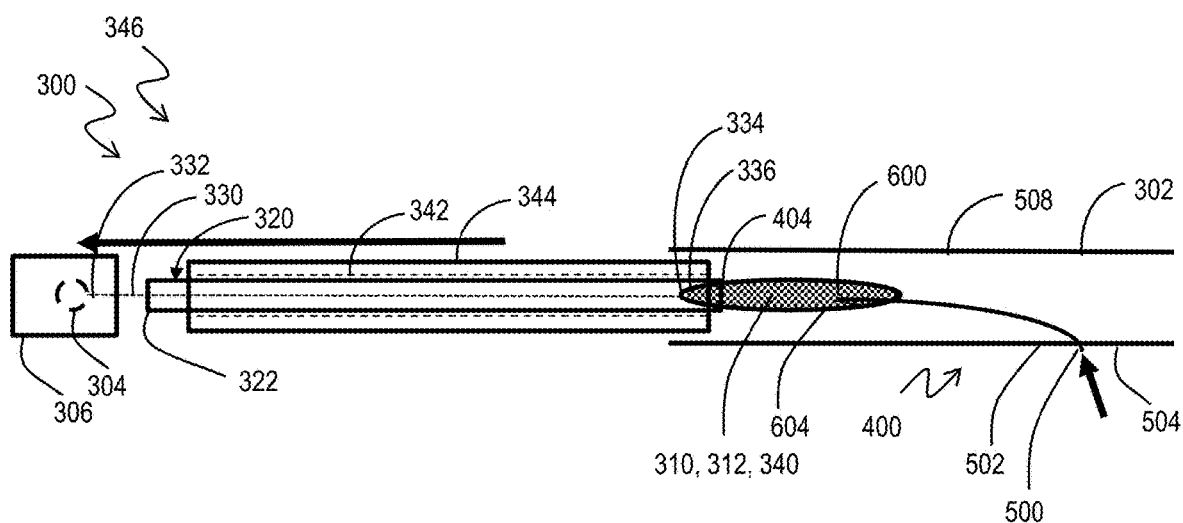
FIG. 7 schematically illustrates a step of retracting the system and wire of FIG. 6 from the esophagus.

FIG. 7 schematically illustrates a step of retracting the system 346 and wire 500 of FIG. 6 from the esophagus 302. The endoscope 344, the partially collapsed expandable mesh 312, and the end 600 of the wire 500 may all be removed simultaneously, while feeding wire 500 through the tracheo-esophageal puncture 502 until the end 600 of the wire 500 protrudes from the oral cavity (not shown). The end 600 of the wire 500 may then be secured to a voice prosthesis insertion apparatus and used to position the voice prosthesis in the tracheo-esophageal puncture 502.

Figure 8:
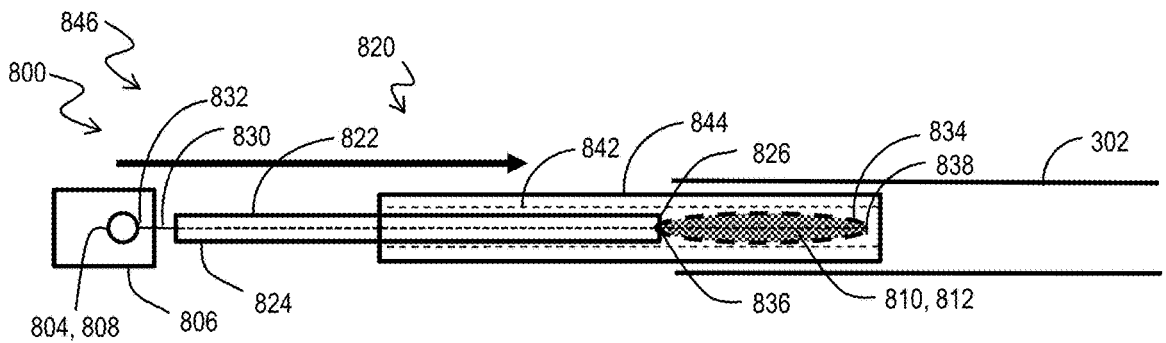
FIG. 8 schematically illustrates a step of inserting an alternate example embodiment of the apparatus into an esophagus.

FIGS. 8-13 schematically illustrate an alternate example embodiment of the apparatus and its use. FIG. 8 schematically illustrates a step of inserting an alternate example embodiment of the apparatus 800 into an esophagus 302. The apparatus 800 includes a movable component 804 initially disposed on a right side of the handle 806 in a second position 808 associated with a collapsed state 810 of the expandable mesh 812. It is noted that the movements and positions of the movable component 804 are purely schematic and may be any type of movement in any direction. The mechanical linkage 820 includes a hollow conduit 822 (e.g. flexible tube) having a proximate end 824 and a distal end 826 and an actuator cable 830. The actuator cable includes a proximate end 832 connected to the movable component 804 and a distal end 834 connected to a distal end 838 of the expandable mesh 812. The proximate end 836 of the expandable mesh 812 abuts the distal end 826 of the hollow conduit 822.

In this example embodiment, the natural state of the expandable mesh 812 is the collapsed state 810. The expandable mesh 812 is disposed in the working channel 842 of the endoscope 844 along with at least a portion of the mechanical linkage 820. In this example embodiment, the expandable mesh is disposed outside of the hollow conduit 822. However, in an alternate example embodiment a separate mesh (not shown) may encircle both the hollow conduit 822 and the expandable mesh 812 and also fit within the working channel 842. In the illustrated embodiment, the sheath does not compress the expandable structure, as id does in FIG. 3, because in FIG. 8 the natural state is collapsed. In various embodiments, the apparatus 800 is inserted into the working channel 842 of the endoscope 844 before, concurrent with, or after the endoscope 844 is inserted into the esophagus 302. It can be seen that when compared to FIG. 3, the mechanical linkage 820 of FIG. 8 is not inserted as far into the working channel 842 to ensure the expandable mesh 812 does not protrude past the distal end of the endoscope 844 when the apparatus 800 and the endoscope 844 are inserted simultaneously. Together the apparatus 800 and the endoscope 844 constitute the system 846

Figure 9:
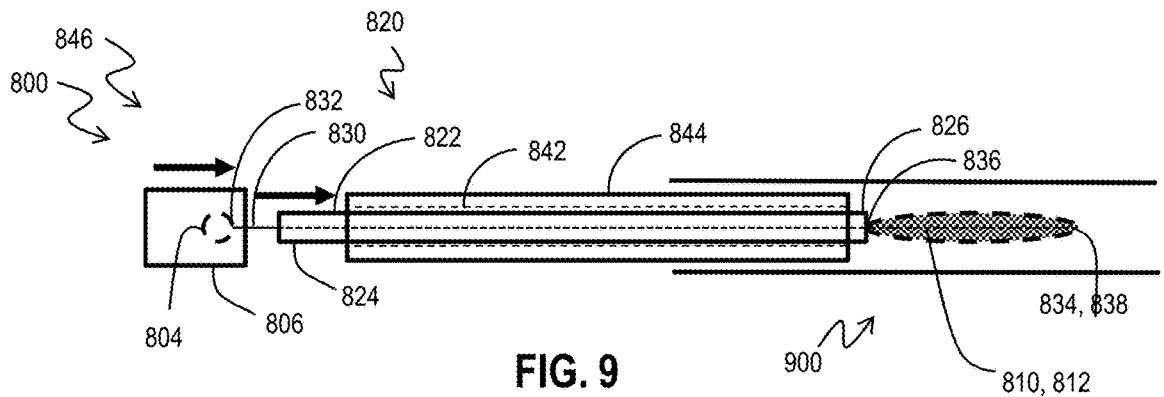
FIG. 9 schematically illustrates a step of moving the apparatus of FIG. 8 through the endoscope of FIG. 8 to expose the expandable mesh.

FIG. 9 schematically illustrates a step of moving the apparatus 800 of FIG. 8 through the endoscope 844 of FIG. 8 to expose the expandable mesh 812. This exposes the expandable mesh 812 at the selected location 900 in the esophagus 302 in the collapsed state 810.

Figure 10:
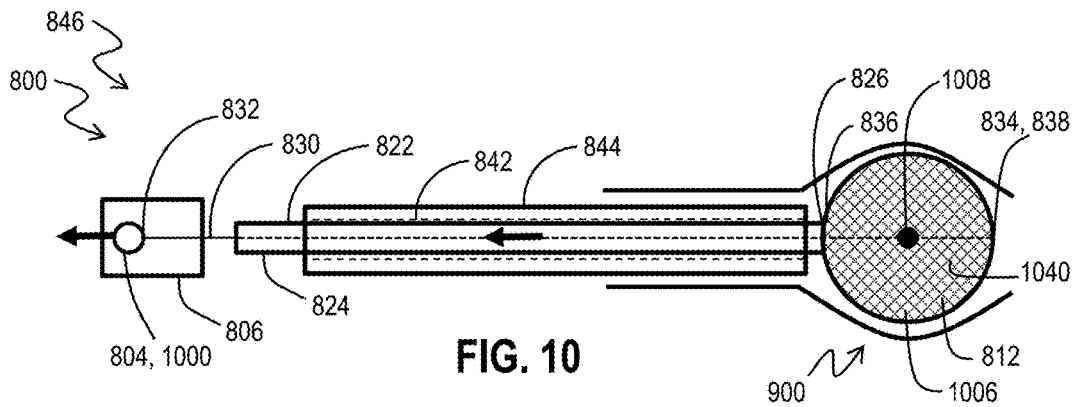
FIG. 10 schematically illustrates a step of expanding the expandable mesh of the apparatus of FIG. 9.

FIG. 10 schematically illustrates a step of expanding the expandable mesh 812 of the apparatus 800 of FIG. 9. The movable component 804 is moved from the second position 808 to the first position 1000. This pulls the actuator cable 830 which, in turn, pulls on the distal end 838 of the expandable mesh 812. The proximate end 836 of the expandable mesh 812 abuts and is held in place by the distal end 826 of the hollow conduit 822. This causes the distal end 838 of the expandable mesh 812 to approach the proximate end 836 of the expandable mesh 812. This, in turn, causes the expandable mesh 812 to expand into its expanded state 1006 against a resilience of the filaments 1040, whereby the esophagus is distended and both walls of the esophagus are supported. As before, a light source 1008 may be disposed in the expandable mesh 812 to aid in visualization of the location of the expandable mesh 812 from outside the esophagus 302.

Figure 11:
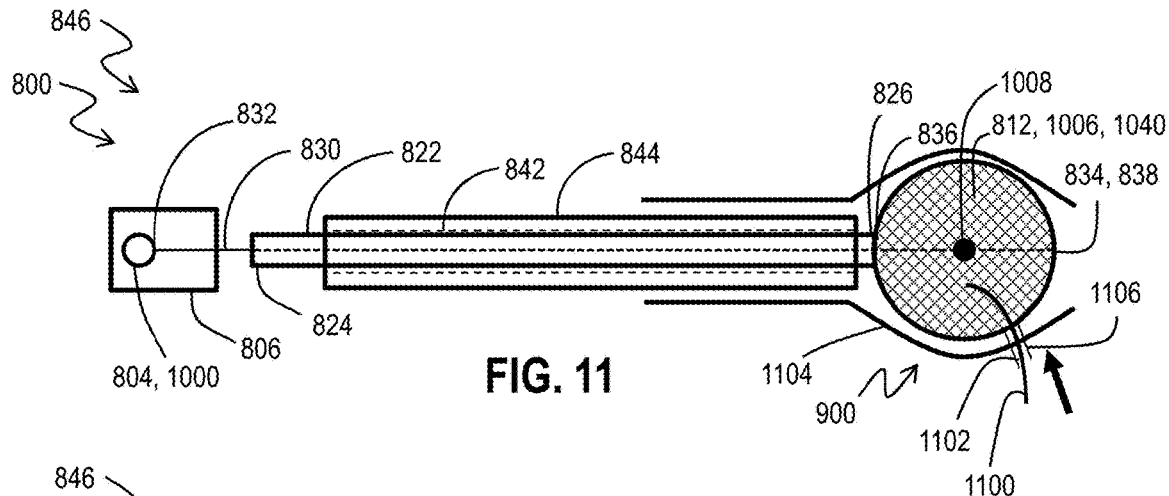
FIG. 11 schematically illustrates a step of inserting of a wire into the expanded expandable mesh of FIG. 10.

FIG. 11 schematically illustrates a step of inserting of a wire 1100 into the expanded expandable mesh 812 of FIG. 10. The wire 1100 is inserted through a tracheo-esophageal puncture 1102 in an anterior wall 1104 of the esophagus 302. As before, in an example embodiment the tracheo-esophageal puncture 1102 is first made using a hollow puncture needle 1106. The wire 1100 is fed into a hollow interior of the puncture needle 1106 until the wire 1100 passes into the expandable mesh 812. In various embodiments, the puncture needle 1106 remains in place or is removed once the wire 1100 is inserted.

Figure 12:
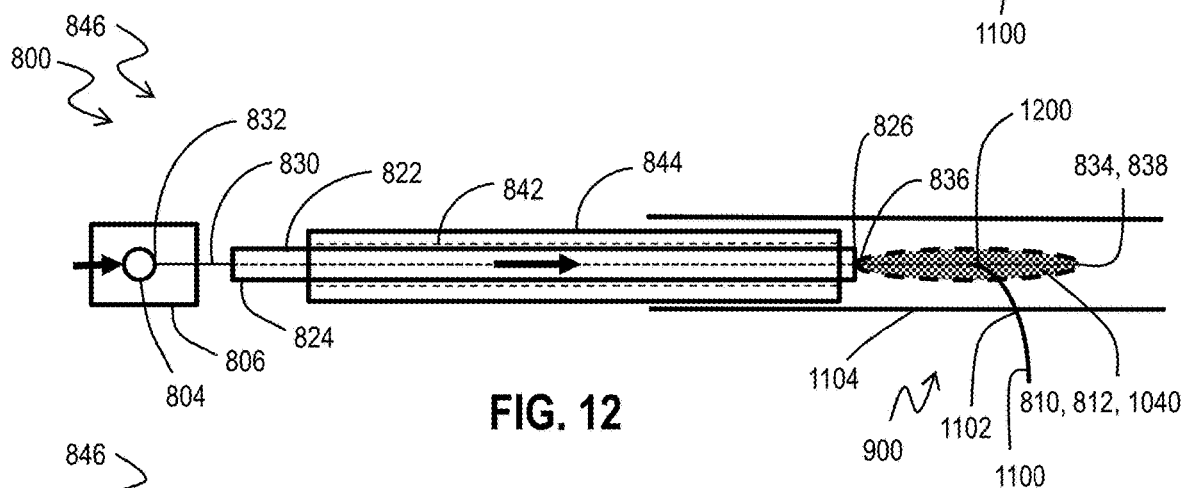
FIG. 12 schematically illustrates a step of collapsing the expandable mesh onto the wire of FIG. 11.

FIG. 12 schematically illustrates a step of collapsing the expandable mesh 812 onto the wire 1100 of FIG. 11. Moving the movable component 804 from the first position 1000 toward the second position 808 pushes on the actuator cable 830. This, in turn, pushes the distal end 838 of the expandable mesh 812 away from the proximate end 836 of the expandable mesh 812, thereby collapsing the expandable mesh 812 and capturing an end 1200 of the wire 1100 therein. In the example embodiment (shown) the movable component 804 does not fully return to the second position 808 because the wire 1100 in the expandable mesh 812 prevents full collapse. However, in an alternate example embodiment the expandable mesh 812 fully collapses. In some embodiments, the puncture needle 1106 is removed at this step.

Figure 13:
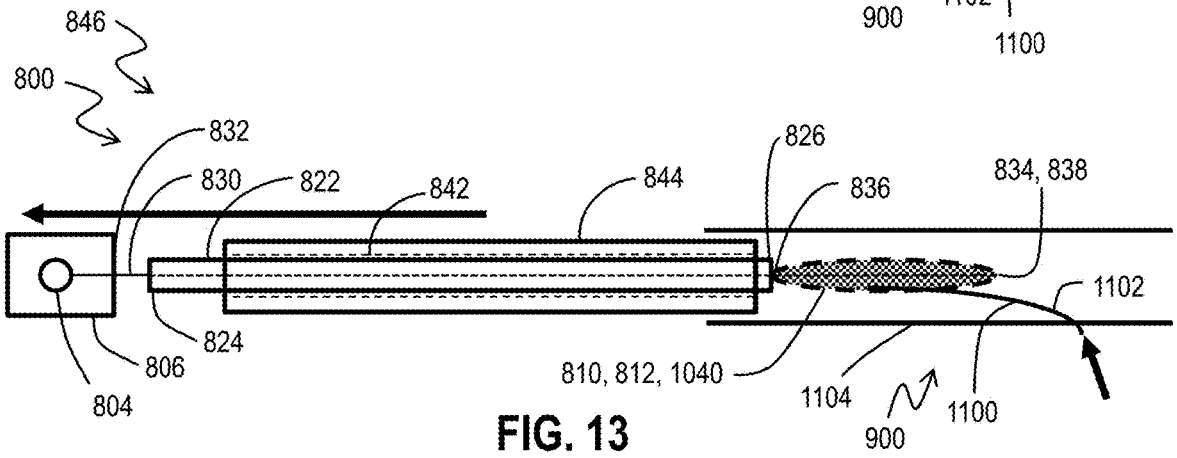
FIG. 13 schematically illustrates a step of retracting the system and wire of FIG. 12 from the esophagus.

FIG. 13 schematically illustrates a step of retracting the system 846 and wire 1100 of FIG. 12 from the esophagus 302. The endoscope 844, the partially or fully collapsed expandable mesh 812, and the end 1200 of the wire 1100 may all be removed simultaneously, while feeding wire 1100 through the tracheo-esophageal puncture 1102 until the end 1200 of the wire 1100 protrudes from the oral cavity (not shown). The end 1200 of the wire 1100 may then be secured to a voice prosthesis insertion apparatus and used to position the voice prosthesis in the tracheo-esophageal puncture 1102.

Figure 14:
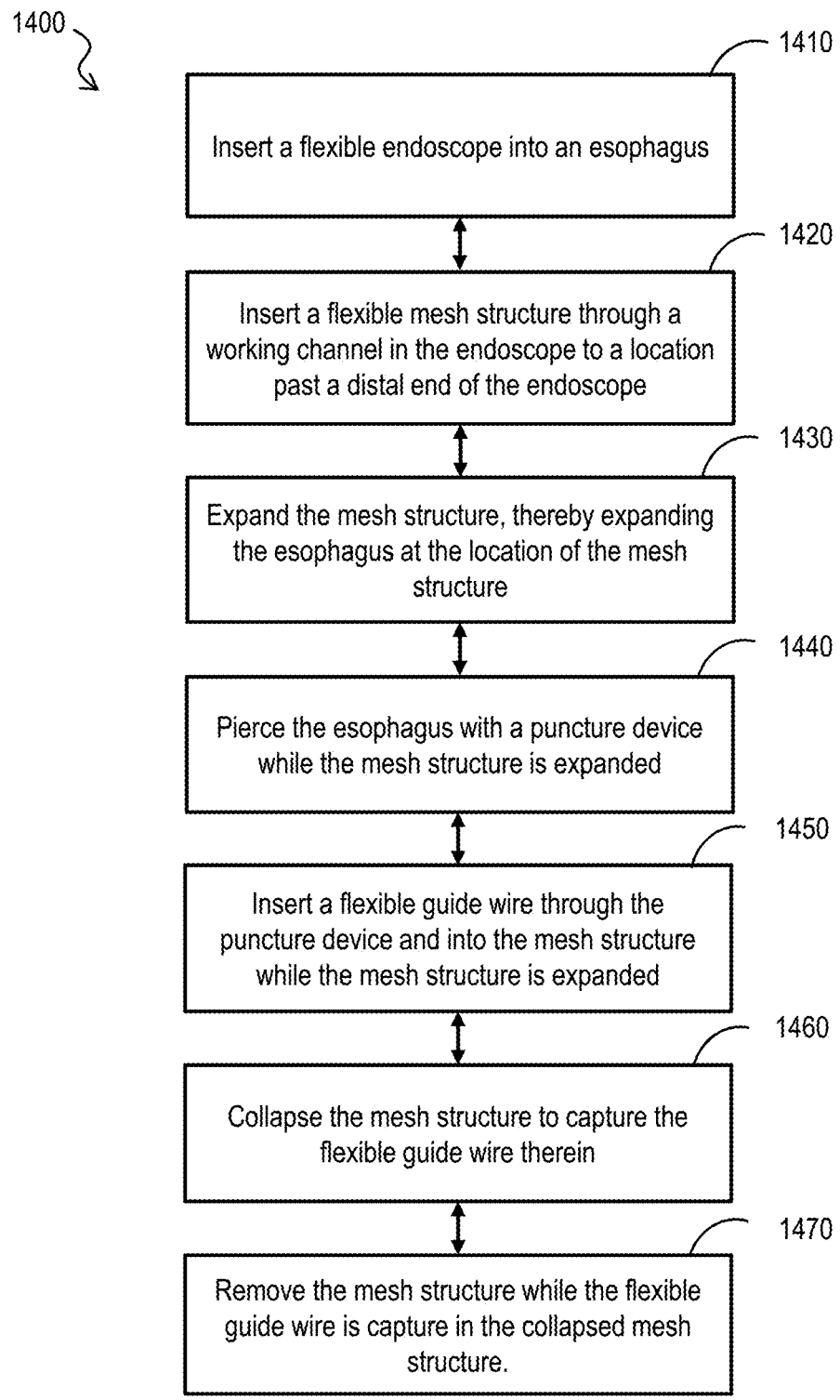
FIG. 14 is a flow chart of an example embodiment of a method of placing a wire through a wall of an esophagus using an example embodiment of the apparatus.

FIG. 14 is a flow chart 1400 that illustrates an example method for using the apparatus to place a wire through a wall of an esophagus using an example embodiment of the apparatus. Step 1410 includes inserting a flexible endoscope into an esophagus. Step 1420 includes inserting an expandable structure though a working channel in the endoscope to a location past a distal end of the endoscope. Step 1430 includes expanding the expandable structure, thereby expanding the esophagus at the location of the expandable structure.

Figure 17A:
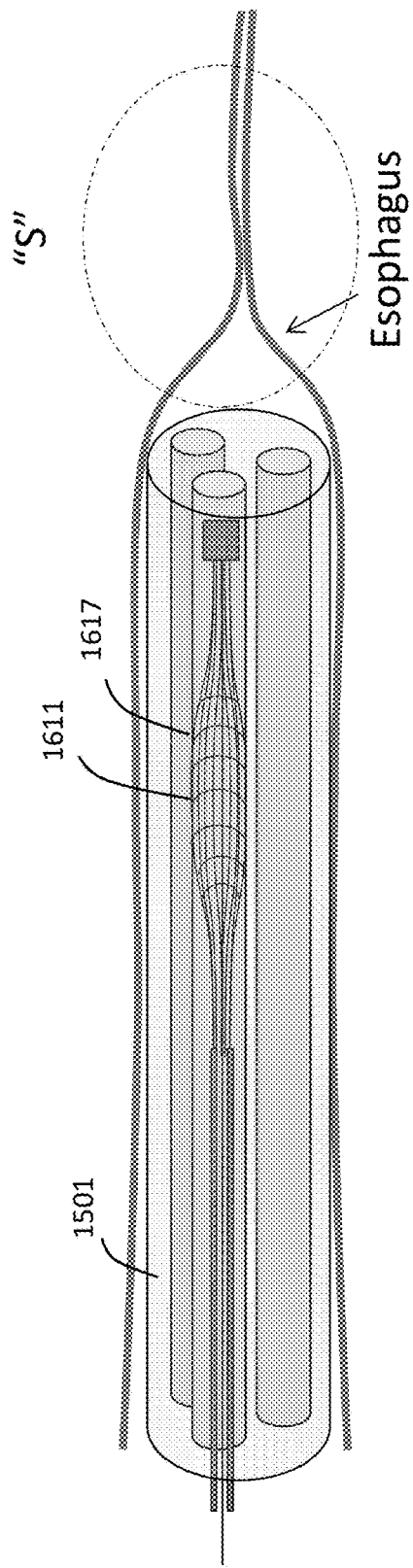
FIG. 17A and FIG. 17B are block diagrams that illustrate an example system using the prior art endoscope of FIG. 15A as inserted in an esophagus prior to and after deployment of the expandable mesh, respectively, according to an embodiment.
Figure 17B:
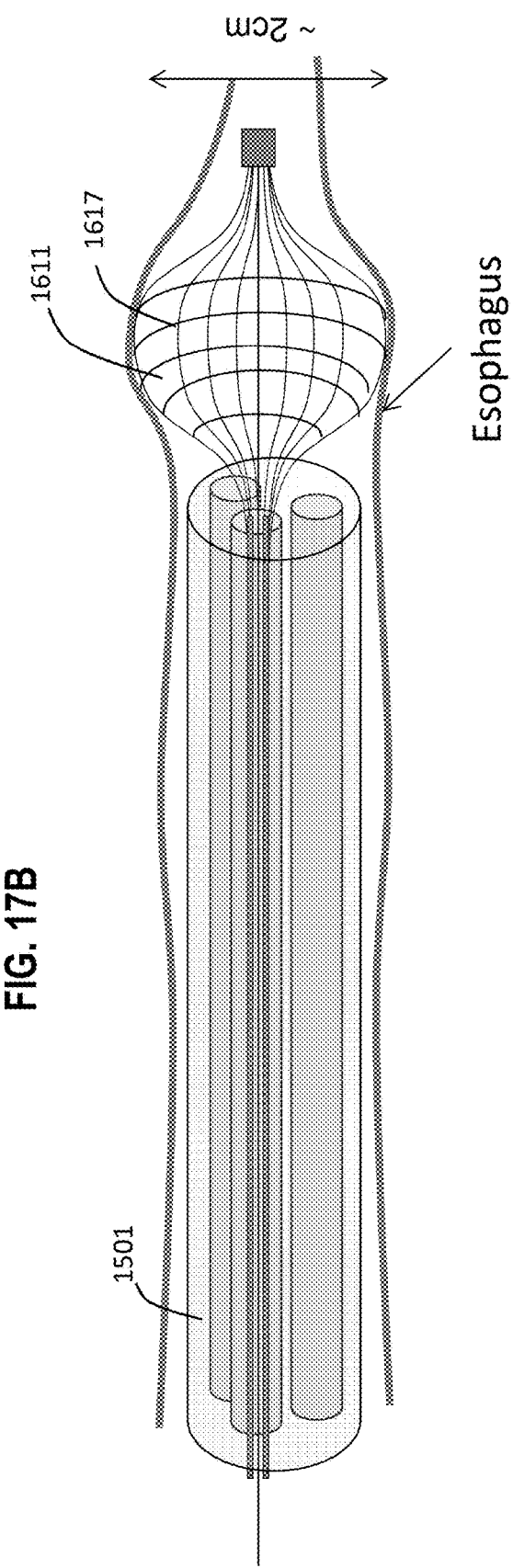

FIG. 17A and FIG. 17B are block diagrams that illustrate an example system using the prior art endoscope 1501 of FIG. 15A as inserted in an esophagus prior to and after deployment of the expandable mesh 1611, respectively, according to an embodiment. This embodiment uses the expandable mesh 1611 with the transverse filaments 1617 of FIG. 16B. FIG. 17A corresponds to step 1410 where S indicates the target positon along the wall of the esophagus where the esophagus is collapsed. FIG. 17B corresponds to step 1430, and shows the esophagus expanded from a collapsed state to open about 2 centimeters at the location of the expandable mesh 1611.

Figure 18A:
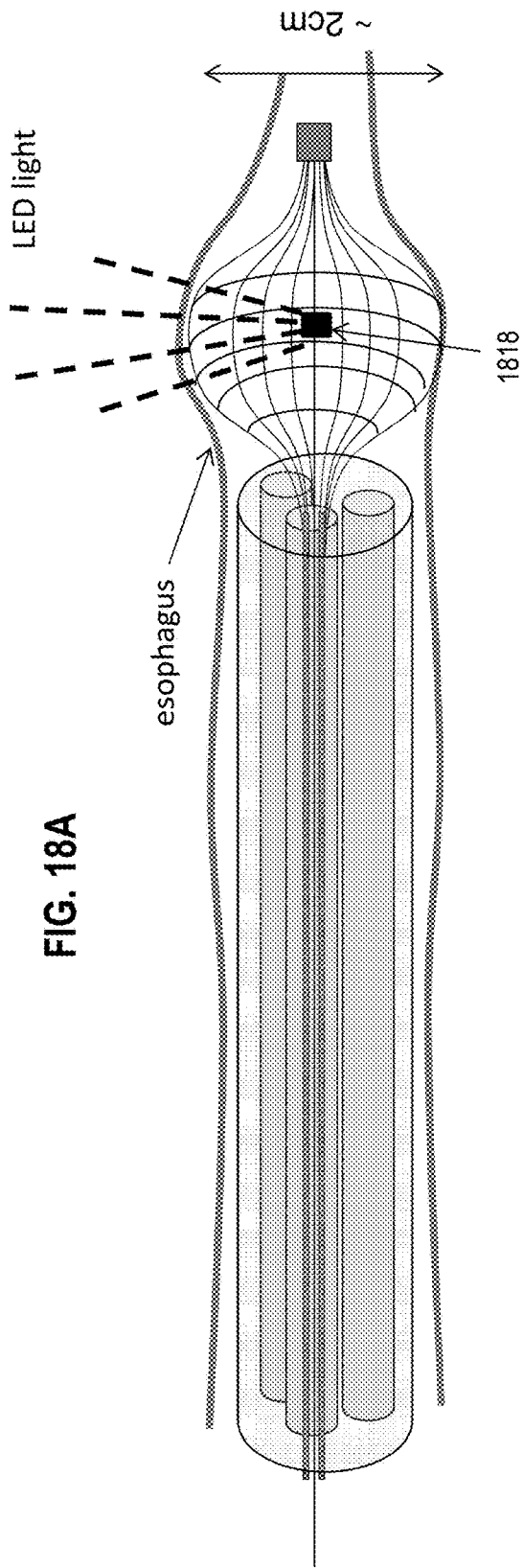
FIG. 18A and FIG. 18B are a block diagrams that illustrate another example system that includes a light source before and after puncturing with a trocar and insertion of a flexible guide wire, according to an embodiment.
Figure 18B:
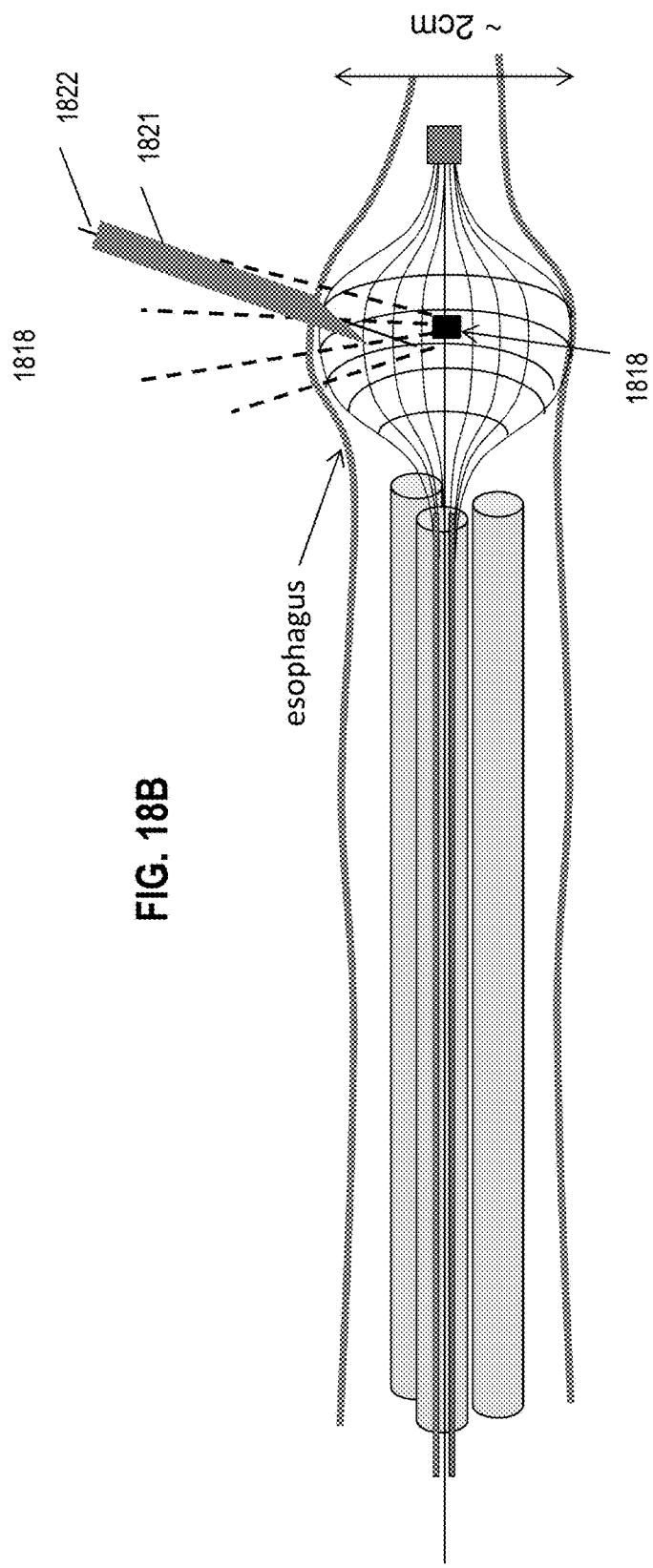

FIG. 18A and FIG. 18B are a block diagrams that illustrates another example system that includes a light source before and after puncturing with a trocar and insertion of a flexible guide wire, respectively, according to an embodiment. In some embodiments, step 1430 includes illuminating a light source to make the location of the expanded mesh visible outside the lumen. FIG. 18A depicts a light emitting diode (LED) 1818 within the expanded mesh.

Figure 19A:
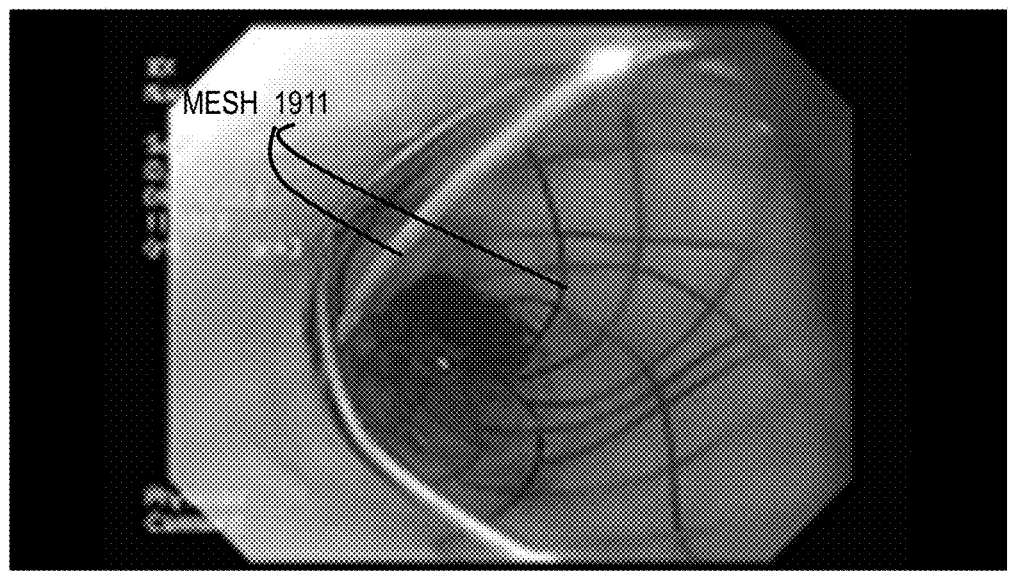
FIG. 19A is a photograph from a camera in a working channel of an endoscope, which illustrates a deployed expanded wire mesh inside the esophagus of a cadaver, according to an embodiment.
Figure 19B:
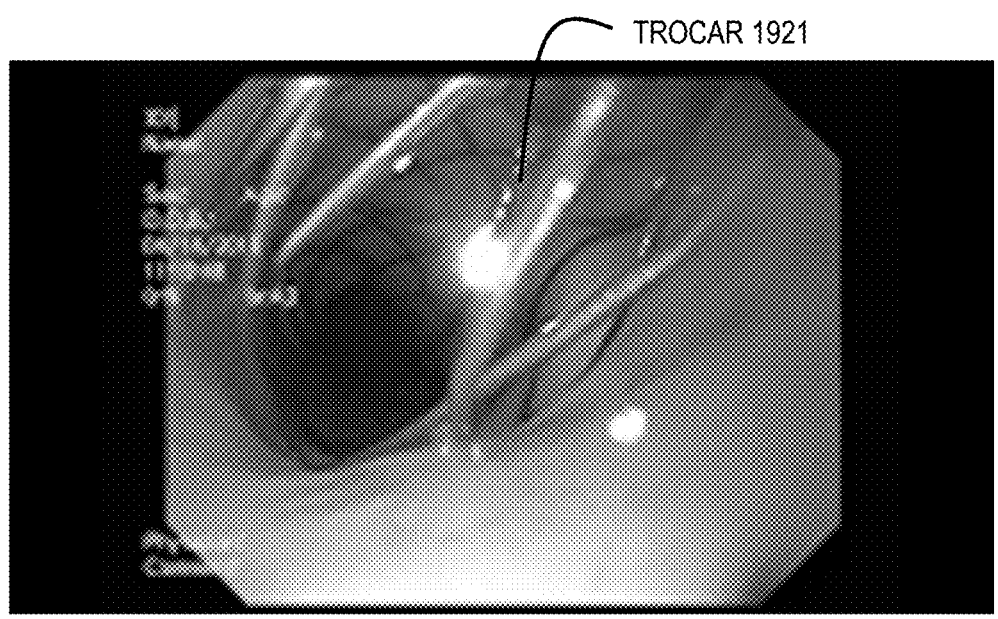
FIG. 19B is a photograph from a camera in a working channel of an endoscope, which illustrates a deployed expanded wire mesh inside the esophagus of a cadaver penetrated by a trocar, according to an embodiment.

Step 1440 includes piercing the esophagus with a puncture device while the mesh structure is expanded. Step 1450 includes inserting a flexible guide wire through the puncture device and into the mesh structure while the mesh structure is expanded. FIG. 18B depicts trocar 1821 puncturing the esophagus at the position of the LED 1818 within the expanded mesh of FIG. 16B as occurs during step 1440 in some embodiments. FIG. 18B depicts a flexible guide wire 1822 inserted through the trocar as occurs during step 1450. FIG. 19A is a photograph from a camera in a working channel of an endoscope, which illustrates a deployed expanded wire mesh 1911 inside the esophagus of a cadaver, according to an embodiment. FIG. 19B is a photograph from a camera in a working channel of an endoscope, which illustrates a deployed expanded wire mesh inside the esophagus of a cadaver penetrated by a trocar 1921, according to an embodiment Step 1460 includes collapsing the mesh structure to capture the flexible guide wire therein. Step 1470 includes removing the mesh structure while the flexible guide wire is capture in the collapsed mesh structure.

Moving a movable component located outside a proximal end of the endoscope in a first direction expands the mesh structure in an example embodiment. Moving the movable component in a second, different direction collapses the mesh structure in an example embodiment. In an example embodiment the mesh structure is expanded by an amount that is proportional to an amount of movement of a movable component in the first direction.

Although steps are depicted in flowchart FIG. 14, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

Figure 20E:
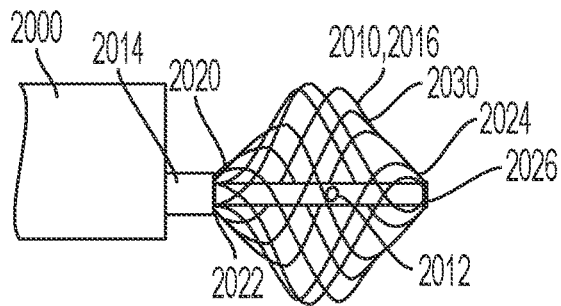

FIG. 20A through FIG. 20F are diagrams that illustrate an example expandable structure using a wire mesh, according to another embodiment. Example dimensions of some components are shown in millimeters. FIG. 20A through FIG.

20C show a perspective view, a cross sectional view, and a side view respectively, showing a flexible endoscope 2000, a working channel 2002, a light channel 2004, and an irrigation channel 2006 of an example embodiment that functions similar to that of FIG. 8 through FIG. 13. Also visible are an expandable structure 2010, an actuator cable 2012, and a hollow conduit 2014. The expandable structure in these example embodiments in an expandable mesh 2016. A proximate end 2020 of the expandable mesh 2016 is secured to a distal end 2022 of the hollow conduit 2014, and a distal end 2024 of the expandable mesh 2016 is secured to a distal end 2026 of the actuator cable 2012.

Figure 20F:
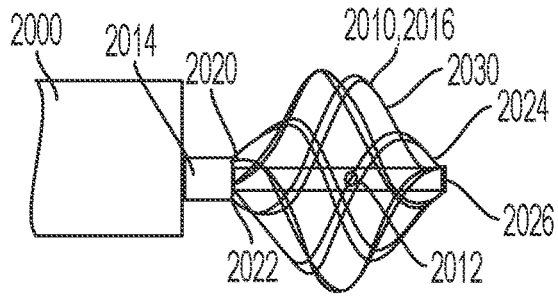

As can be seen in FIG. 20D through FIG. 20F, movement of the actuator cable 2012 to the left (as seen on the page in FIG. 20E through FIG. 20F) moves the distal end 2024 of the expandable mesh 2016 toward the proximate end 2020 of the expandable mesh 2016. The causes the filaments 2030 to bow outward, thereby increasing the diameter of the expandable mesh 2016. Oppositely, movement of the actuator cable 2012 to the right (as seen on the page in FIG. 20E through FIG. 20F) moves the distal end 2024 of the expandable mesh 2016 away from the proximate end 2020 of the expandable mesh 2016, thereby collapsing the expandable mesh 2016. In the example embodiment of FIG. 20D through FIG. 20F, some filaments 2030 spiral in one direction and other filaments spiral in the other direction around the actuator cable 2012.

While not illustrated, it is possible for the expandable meshes 2016 of FIG. 20D through FIG. 20F to operate similar to the example embodiments of FIG. 3 through FIG. 7. In such embodiments, the expandable mesh 2016 would be held in a collapsed state within a sheath and could be pushed out a distal end of the sheath via the actuator cable, during which time the expandable mesh 2016 would then expand under its own resilience.

Figure 21A:
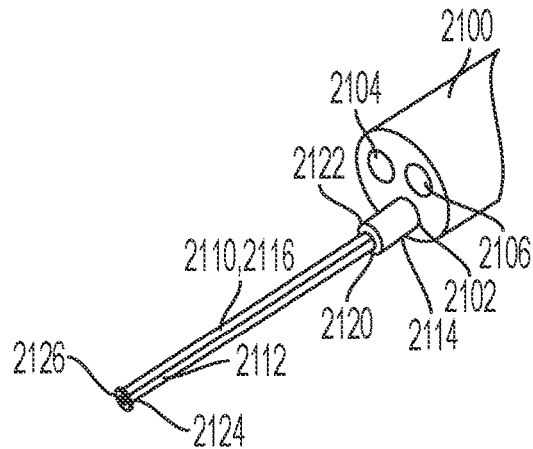
FIG. 21A through FIG. 21F are diagrams that illustrate an example expandable structure using stiff ribbons, according to another embodiment.
Figure 21B:
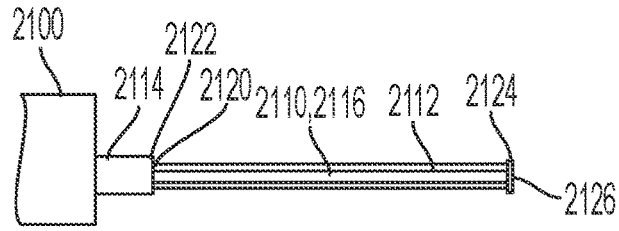
Figure 21C:
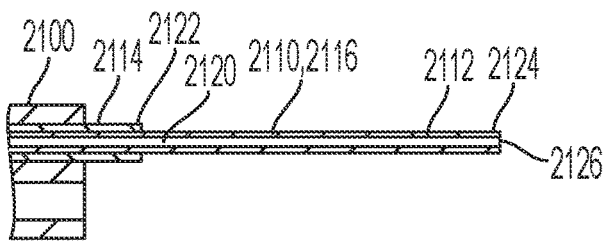

FIG. 21A through FIG. 21F are diagrams that illustrate an example expandable structure using broad filaments, according to another embodiment. Example dimensions of some components are shown in millimeters. When made of the same material as the thin filaments, these broad filaments were found to offer an advantage of exerting greater force and therefore found to be more effective at expanding the body lumen for a particular filament material. FIG. 21A through FIG. 21C show a perspective view, a cross sectional view, and a side view respectively, showing a flexible endoscope 2100, a working channel 2102, a light channel 2104, and an irrigation channel 2106 of an example embodiment that functions similar to that of FIG. 8 through FIG. 13. Also visible are an expandable structure 2110, an actuator cable 2112, and a hollow conduit 2114. The expandable structure 2110 in these example embodiments includes broad filaments 2116. The broad filaments may be any form of discrete elongated structure wider than thick that may bow outward, such as stiff ribbons, as shown. The broad filaments 2116 in this example embodiment do not crisscross each other along the actuator cable 2112, whether in an expanded or collapsed state but remain co-planar with the actuator cable. In other embodiments, the broad filaments 2116 may take a helical/corkscrew shape, or any other shape of interest relative to the actuator cable 2112, in the expanded and/or collapsed states. A proximate end 2120 of each broad filament 2116 is secured to a distal end 2122 of the hollow conduit 2114, and a distal end 2124 of each broad filament 2116 is secured to a distal end 2126 of the actuator cable 2112.

Figure 21D:
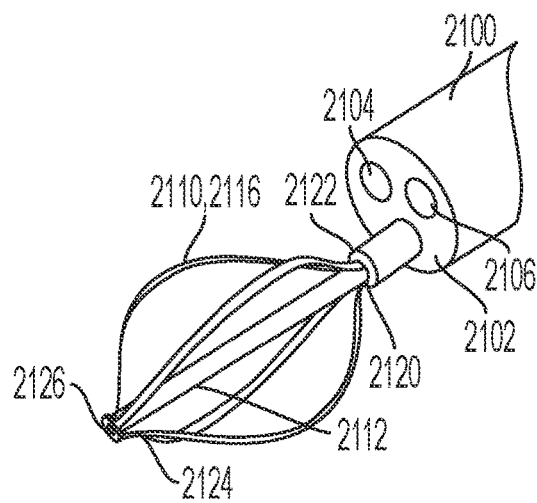
Figure 21E:
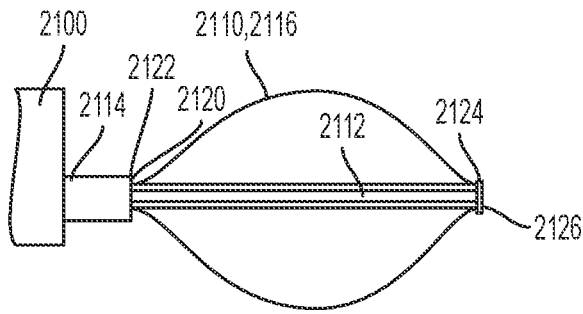
Figure 21F:
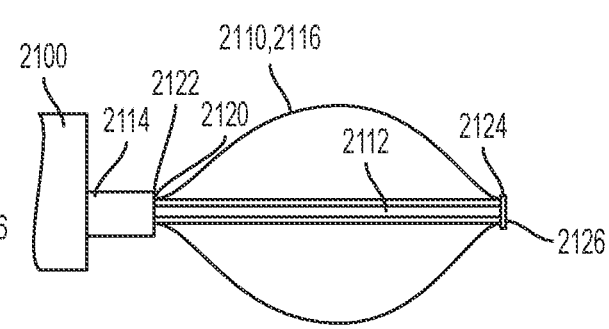

As can be seen in FIG. 21D through FIG. 21F, movement of the actuator cable 2112 to the left (as seen on the page in FIG. 21E through FIG. 21F) moves the distal ends 2124 of the broad filaments 2116 toward the proximate ends 2120 of the filaments 2116. This causes the broad filaments 2116 to bow outward, thereby increasing the diameter of the expandable structure 2110. Oppositely, movement of the actuator cable 2112 to the right (as seen on the page in FIG. 21E through FIG. 21F) moves the distal end 2124 of the filaments 2116 away from the proximate end 2120 of the filaments 2116, thereby releasing the bow of the broad filaments 2116 and collapsing the expandable structure 2110. Releasing the bow of the broad filaments 2116 is understood to mean collapsing the broad filaments 2116, and collapsing the broad filaments 2116 is synonymous with collapsing the expandable structure 2110.

While not illustrated, it is possible for the broad filaments 2116 of FIG. 21D through FIG. 21F to operate similar to the example embodiments of FIG. 3 through FIG. 7. In such embodiments, the broad filaments 2116 would be held in a collapsed state within a sheath and could be pushed out a distal end of the sheath via the actuator cable, during which time the broad filaments 2116 would then expand under their own resilience.

Figure 22A:
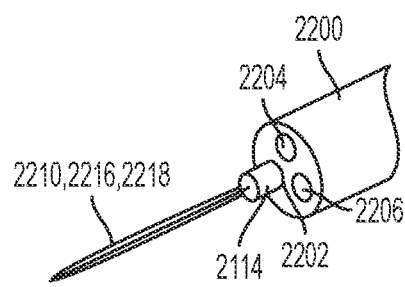
FIG. 22A through FIG. 22F are diagrams that illustrate an example expandable structure using a single stiff strand, according to another embodiment.
Figure 22B:
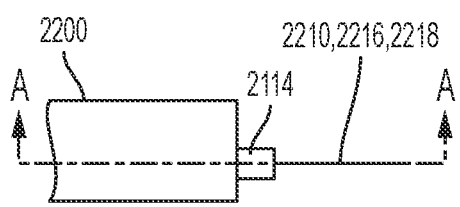
Figure 22C:
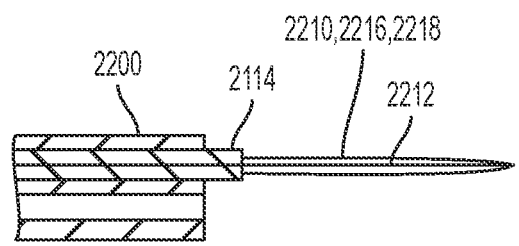

FIG. 22A through FIG. 22F are diagrams that illustrate an example expandable structure using a single stiff strand, according to another embodiment. Example dimensions of some components are shown in millimeters. FIG. 22A through FIG. 22C show a perspective view, a cross sectional view, and a side view respectively, showing a flexible endoscope 2200, a working channel 2202, a light channel 2204, and an irrigation channel 2206 of an example embodiment that functions similar to that of FIG. 8 through FIG. 13. Also visible are an expandable structure 2210, an actuator cable 2212, and a hollow conduit 2214. The expandable structure 2210 in these example embodiments includes a strand 2216. The strand may be any form of discrete elongated structure that may be bent, such as a stiff ribbon as shown, or plural wires braided together etc. The strand 2216 in this example embodiment forms a single loop 2218. The actuator cable 2212 is secured to a point 2220 on the strand 2216. The point 2220 separates the strand 2216 into two filaments 2222, 2224, each having a proximate end 2230 secured to a distal end 2232 of the hollow conduit 2214, and a distal end 2234 secured to a distal end 2236 of the actuator cable 2212.

Figure 22D:
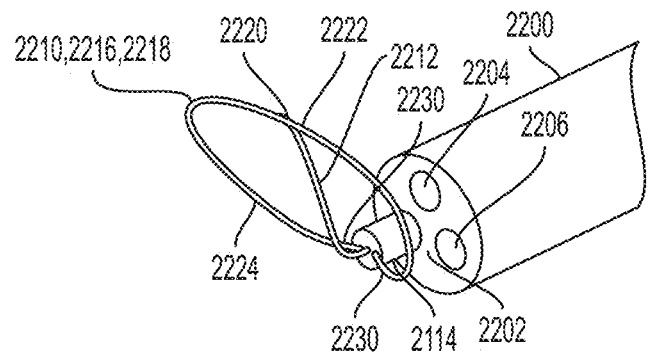
Figure 22E:
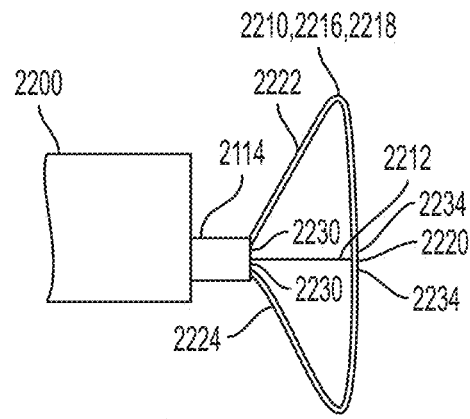
Figure 22F:
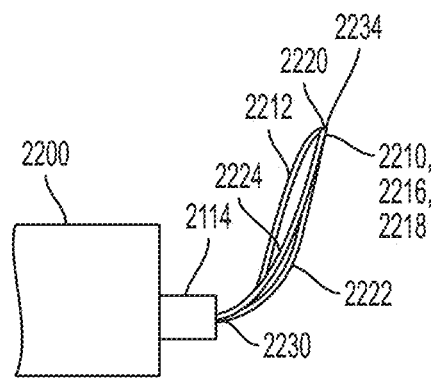

As can be seen in FIGS. 22D-22F, movement of the actuator cable 2112 to the left (as seen on the page in FIGS. 22E-22F) moves the distal ends 2134 of the filaments 2222, 2224 toward the proximate ends 2230 of the filaments 2222, 2224. The causes the filaments 2222, 2224 to bow outward, thereby increasing the diameter of the expandable structure 2110 by forming the loop 2218. Oppositely, movement of the actuator cable 2112 to the right (as seen on the page in FIGS. 22E-22F) moves the distal end 2134 of the filaments 2222, 2224 away from the proximate end 2230 of the filaments 2222, 2224, thereby releasing the bow of the filaments 2222, 2224 and collapsing the expandable structure 2210 and loop 2218. Releasing the bow of the filaments 2222, 2224 is understood to mean collapsing the filaments 2222, 2224, and collapsing the filaments 2222, 2224 is synonymous with collapsing the expandable structure 2210 and the loop 2218.

Figure 23A:
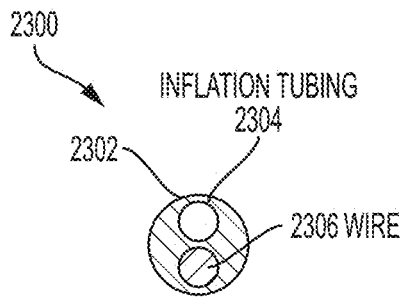
FIG. 23A through FIG. 23F are diagrams that illustrate various example expandable structures using a balloon, according to other embodiments.
Figure 23B:
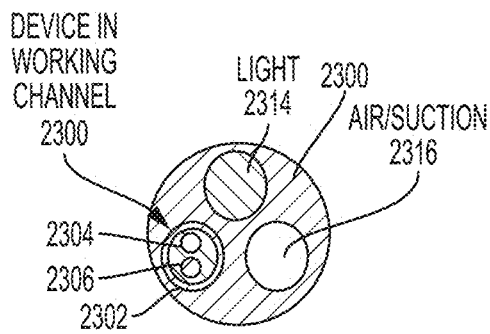

FIG. 23A through FIG. 23F are diagrams that illustrate various example expandable structures using a balloon, according to other embodiments. FIG. 23A shows a mechanical linkage 2300 including a housing 2302 having a tubing passage 2304 and a cable passage 2306. FIG. 23B shows the mechanical linkage 2300 disposed in a working channel 2310 of a flexible endoscope 2312 also having a light channel 2314 and an irrigation channel 2316.

Figure 23C:
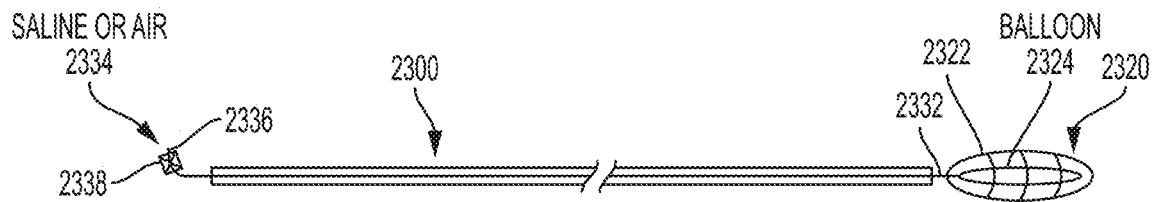
Figure 23D:
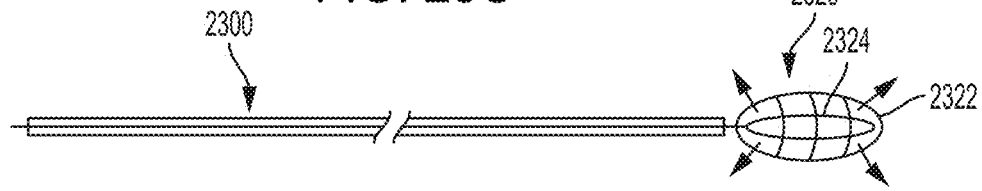

FIG. 23C schematically shows a side view of the mechanical linkage 2300 having an expandable structure 2320 that includes filaments 2322 and an inflatable element 2324 disposed inside the filaments 2322. The inflatable element 2324 may be a balloon used in surgical environments or comparable. The filaments 2322 may form an expandable mesh, or may be broad filaments as in FIG. 21A through FIG. 21F that do not crisscross, such as bands or ribbons. The inflatable element 2324 is disposed inside the filaments 2322 so that inflation of the inflatable element 2324 expands the filaments 2322, as can be seen in FIG. 23D. A fluid tube 2330 disposed in the tubing passage 2304 and a distal end 2332 of the fluid tube 2330 is connected to the inflatable element 2324 to provide fluid communication to the inflatable element 2324 to inflate and deflate it. A source 2334 of a fluid, which may be a liquid or a gas, is connected to a proximal end 2336 of the fluid tube 2330, optionally through a valve 2338.

In one example embodiment, the filaments 2322 remain entirely within their elastic deformation range during operation. Accordingly, when the inflatable element 2324 is inflated the filaments 2322 expand. Likewise, when the inflatable element 2324 is deflated the filaments 2322 collapse. This natural collapsing of the filaments 2322 will capture any guide wire that has been inserted between the filaments 2322.

Figure 23E:
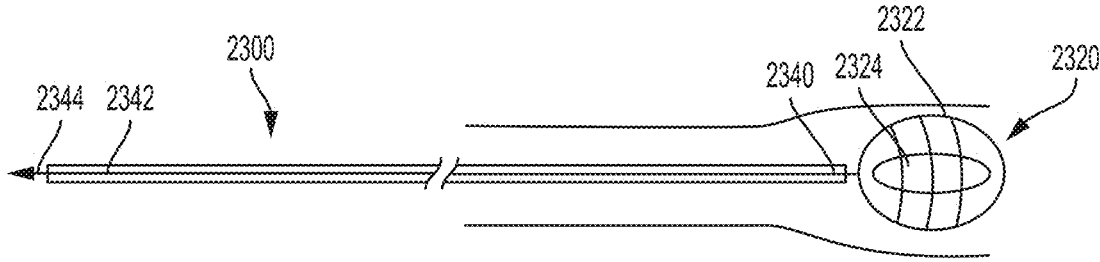

In another example embodiment, shown in FIG. 23E, the filaments 2322 do not remain entirely within their elastic range during operation. Instead, the inflatable element expands the filaments 2322 beyond their elastic range so that the filaments 2322 remain expanded even when the inflatable element 2324 deflates inside the filaments. In this embodiment, the inflatable element 2324 can be removed simply by pulling on the fluid tube and pulling the balloon out through the tube passage 2304. The filaments 2322 are secured to a distal end 2340 of the cable 2342, which is disposed in the cable passage 2306. To collapse the expanded and rigid filaments 2322, a proximate end 2344 of the cable 2342 can be pulled, which will forcefully draw the expanded, rigid filaments 2322 into the cable passage, collapsing them in the process. This forced collapsing of the filaments 2322 will capture any guide wire that has been inserted between the filaments 2322.

Figure 23F:
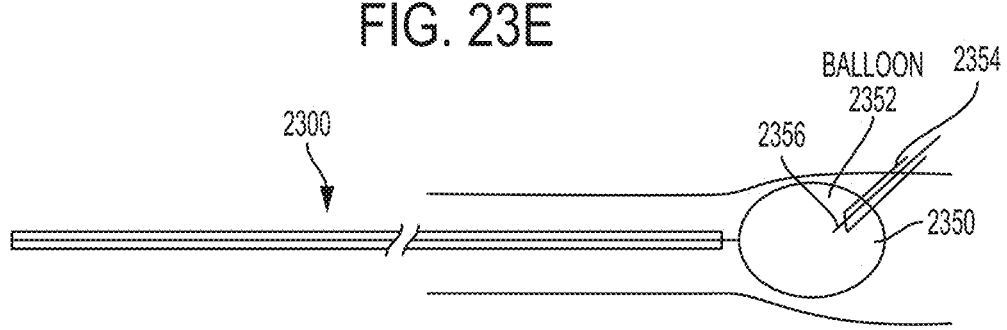

In another example embodiment, shown in FIG. 23F, no filaments 2322 are present. Instead, the expandable structure 2350 is limited to the inflatable element 2352. A hollow puncture needle 2354 may pierce the inflatable element 2352 without collapsing it when the inflatable element 2352 is the self-healing type. The amount of friction provided in such an inflatable element 2352 is sufficient to trap and retain an inserted guide wire 2356 upon deflation of the inflatable element.

FIG. 24A through 24C are diagrams that illustrate an example expandable structure having backside protection, according to another embodiment. FIG. 24A shows an expandable structure 2400 that operates like the embodiment shown in FIGS. 3-13. As shown, the expandable structure 2400 is in an expanded state 2402. FIG. 24B is a cross section taken along line A-A of FIG. 24A showing the filaments 2404 and the actuator cable 2406. In this embodiment, a distribution of the filaments 2404 is not uniform in the circumferential direction 2410. Instead, there is a first circumferential region 2412 and a second circumferential region 2414. In the first circumferential region 2412 the expandable structure 2400 is configured to provide minimal obstruction to an objected being inserted there through. This may be accomplished in various ways. In the embodiment shown, the filaments 2404 occupy a relatively small portion of the first circumferential region 2412, thereby leaving relatively large gaps 2420 between the filaments 2404. In the second circumferential region 2414 the filaments 2404 occupy a relatively larger portion of the second circumferential region 2414, thereby leaving relatively small gaps 2422 there between.

In operation, an object such as a trocar or a guide wire may be inserted into the expandable structure 2400 relatively easily through the first circumferential region 2412. However, in the event the object is inserted farther, the object will reach the second circumferential region 2414, where the object stands a greater chance it will be blocked by the less porous second circumferential region 2414. Blocking the object in this manner will mitigate the chances that the object will pass fully through the expandable structure 2400. This protects any tissue that may be adjacent the second circumferential region 2414 of the expandable structure 2400, such as a back (far) wall of the esophagus.

FIG. 24C shows the expandable structure 2400 in a collapsed state 2430. In this embodiment, the greater population density of the filaments 2404 and/or the wider widths of the filaments 2404 in the second circumferential region 2414 are accommodated by allowing the collapsed filaments 2404 to stack on each other. This permits the expandable structure 2400 to collapse to a size that is small enough to fit into the working channel Various other shapes may be used for the expandable structure 2400 in order to provide greater access to an object in the first circumferential region 2412 and less in the second circumferential region 2414.

From the foregoing it can be seen that the inventor has devised an apparatus and a method that make tracheo-esophageal puncture procedures possible for patients previously unsuited for the procedure, that increases accurate placement of the tracheo-esophageal puncture, and that reduces chances of collateral harm to the esophagus. Accordingly, it represents an improvement in the art.

The invention claimed is:

1. An apparatus, comprising:
   an expandable structure that can be formed into three dimensional shapes comprising a range of diameters and corresponding lengths;
   a movable component that is movable between a range of positions effecting the range of diameters; and
   a mechanical linkage disposed between the movable component and the expandable structure;
   wherein the expandable structure is configured to fit inside a working channel of an endoscope when the expandable structure is collapsed;
   wherein the mechanical linkage is configured to move a collapsed expandable structure through the working channel to a selected location past a distal end of the endoscope, the mechanical linkage further comprising an actuator cable secured to a distal end of the expandable structure, wherein the actuator cable is configured to be pulled to effect movement of the distal end of the expandable structure toward a proximal end of the expandable structure to expand the expandable structure and the actuator cable is configured to be pushed to effect movement of the distal end of the expandable structure away from the proximal end to collapse the expandable structure in response to movement of the movable component;
   wherein the expandable structure is not uniformly distributed in a circumferential direction such that a first gap is provided in a first circumferential region of the expandable structure and a second gap is provided in a second circumferential region wherein the second gap is smaller than the first gap to facilitate insertion of a guidewire through the first gap in the first circumferential region and block the guidewire from passing through the second gap in the second circumferential region;

wherein the first circumferential region comprises a plurality of first filaments that define a first arcuate shape;

wherein the second circumferential region comprise a plurality of second filaments that define a second arcuate shape; and wherein each of the plurality of second filaments are circumferentially wider than each of the plurality of first filaments in the circumferential direction such that the second gap between adjacent second filaments of the plurality of second filaments is smaller than the first gap between adjacent first filaments of the plurality of first filaments.

2. The apparatus of claim 1, the mechanical linkage further comprising a hollow conduit surrounding the actuator cable and secured to the proximal end of the expandable structure, wherein movement of the actuator cable relative to the hollow conduit in one direction expands the expandable structure, and movement of the actuator cable relative to the hollow conduit in an opposite direction collapses the expandable structure.

3. The apparatus of claim 1, wherein the endoscope comprises a flexible endoscope, and wherein the mechanical linkage is characterized by a resilience that enables the mechanical linkage to flex with the flexible endoscope.

4. The apparatus of claim 2, wherein the expandable structure comprises plural parallel filaments, each filament connected at a distal end to the actuator cable and at a proximate end to the hollow conduit.

5. The apparatus of claim 4, wherein each filament is configured to bow outward relative to the actuator cable when the actuator cable is pulled to expand the expandable structure.

6. An apparatus, comprising:
an expandable structure comprising broad filaments that are formable into three dimensional shapes comprising a range of diameters and corresponding lengths;
a movable component that is moveable between a range of positions effecting the range of diameters; and
a mechanical linkage disposed between the movable component and the expandable structure;
wherein the expandable structure is configured to fit inside a working channel of an endoscope when the broad filaments are collapsed;
wherein the mechanical linkage is configured to move the expandable structure through the working channel to a selected location past a distal end of the endoscope when the broad filaments are collapsed, and to increase and decrease a diameter defined by the broad filaments in response to changes in a position of the movable component within the range of positions when the expandable structure is at the selected location;
wherein the broad filaments of the expandable structure are not uniformly distributed in a circumferential direction such that a first gap is provided between the broad filaments in a first circumferential region of the expandable structure and a second gap is provided between the broad filaments in a second circumferential region wherein the second gap is smaller than the first gap to facilitate insertion of a guidewire through the first gap in the first circumferential region and block the guidewire from passing through the second gap in the second circumferential region;

wherein the broad filaments in the first circumferential region define a first arcuate shape;

wherein the broad filaments in the second circumferential region define a second arcuate shape; and wherein the broad filaments in the second circumferential region are circumferentially wider than each of the broad filaments in the first circumferential region such that the second gap is smaller than the first gap.

7. The apparatus of claim 6, the mechanical linkage further comprising an actuator cable and a hollow conduit surrounding the actuator cable,
wherein each broad filament comprises a distal end secured to the actuator cable and a proximate end configured to be held in a fixed position relative to the hollow conduit, and
wherein movement of the actuator cable relative to the hollow conduit in one direction in response to a first movement of the movable component effects the increase in the diameter defined by the broad filaments, and movement of the actuator cable relative to the hollow conduit in an opposite direction in response to a second movement of the movable component effects the decrease the diameter defined by the broad filaments.

8. The apparatus of claim 7, wherein the broad filaments remain uncrossed with each other whether the broad filaments are expanded or collapsed.

9. The apparatus of claim 8, wherein the broad filaments comprise plural parallel broad filaments configured to bow outwards to increase the diameter defined by the broad filaments.

10. A system, comprising:
a flexible endoscope comprising a working channel;
an expandable structure;
a handle; and
a flexible mechanical linkage disposed between the handle and the expandable structure and configured to deliver the expandable structure through the working channel to a location beyond the working channel, the mechanical linkage comprising a flexible actuator cable secured to a distal end of the expandable structure and configured to be pulled to effect movement of the distal end toward a proximal end of the expandable structure to expand the expandable structure and to be pushed to effect movement of the distal end away from the proximal end to collapse the expandable structure, wherein collapsing the expandable structure is effective to capture an object disposed in an opening of the expandable structure; and wherein the expandable structure is not uniformly distributed in a circumferential direction such that a first gap is provided in a first circumferential region of the expandable structure comprising a plurality of first filaments that define a first arcuate shape and a second gap is provided in a second circumferential region comprising a plurality of second filaments that define a second arcuate shape; and wherein each of the plurality of second filaments are circumferentially wider than each of the plurality of first filaments in the circumferential direction such that the second gap between adjacent second filaments of the plurality of second filaments is smaller than the first gap between adjacent first filaments of the plurality of first filaments to facilitate insertion of a guidewire through the first gap in the first circumferential region and block the guidewire from passing through the second gap in the second circumferential region.

11. The system of claim 10, wherein a magnitude of expansion of the expandable structure is proportional to a magnitude of movement of the mechanical linkage in a first direction, and a magnitude of a collapse of the expandable structure is proportional to a magnitude of movement of the mechanical linkage in a second direction.

12. The system of claim 10, wherein the expandable structure comprises plural filaments disposed circumferentially about the mechanical linkage, each filament connected at a distal end of the filament to the mechanical linkage.

13. The system of claim 12, wherein between the distal end and a proximate end, each filament is free of direct connection with all other filaments of the plural filaments.

14. A method, comprising:
inserting a flexible endoscope into a body lumen of a subject;
inserting an expandable structure comprising broad filaments through a working channel in the endoscope to a location past a distal end of the endoscope;
expanding the expandable structure by moving a movable component located outside a proximal end of the endoscope in a first direction to pull a distal end of the expandable structure toward a proximate end of the expandable structure at the location of the expandable structure, wherein the broad filaments of the expanded expandable structure are not uniformly distributed in a circumferential direction such that a first gap is provided between the broad filaments in a first circumferential region of the expandable structure that have a first arcuate shape and a second gap is provided between the broad filaments in a second circumferential region that have a second arcuate shape, wherein the broad filaments in the second circumferential region are circumferentially wider than the broad filaments in the first circumferential region such that the second gap is smaller than the first gap; and
inserting a flexible guide wire through the first gap in the first circumferential region of the expandable structure and blocking the flexible guide wire from passing through the second gap in the second circumferential region of the expandable structure.

15. The method of claim 14, wherein the body lumen is an esophagus and the method further comprises piercing the esophagus with a puncture device while the expandable structure is expanded.

16. The method of claim 15, further comprising inserting the flexible guide wire through the puncture device and into the expandable structure through the first gap while the expandable structure is expanded.

17. The method of claim 16, further comprising collapsing the expandable structure to capture the flexible guide wire therein by moving the movable component in a second direction to push the distal end of the expandable structure away from the proximate end of the expandable structure.

18. The method of claim 17, further comprising retracting the expandable structure from the body lumen while the flexible guide wire is captured in the collapsed expandable structure.

19. The method of claim 14, wherein the expandable structure comprises plural broad filaments disposed in an annular arrangement, each filament being configured to bow outward when the movable component is moved in the first direction.

* * * * *